US009506086B2

(12) United States Patent
Jannson et al.

(10) Patent No.: US 9,506,086 B2
(45) Date of Patent: Nov. 29, 2016

(54) MICROORGANISMS FOR BIOSYNTHESIS OF LIMONENE ON GASEOUS SUBSTRATES

(71) Applicant: Kiverdi, Inc., Berkeley, CA (US)

(72) Inventors: Christer Jannson, Berkeley, CA (US); Cody A. Marcus Carr, Berkeley, CA (US); John S. Reed, Berkeley, CA (US)

(73) Assignee: Kiverdi, Inc., Hayward, CA (US)

( * ) Notice: Subject to any disclaimer, the term of this patent is extended or adjusted under 35 U.S.C. 154(b) by 0 days.

(21) Appl. No.: 14/706,932

(22) Filed: May 7, 2015

(65) Prior Publication Data
US 2015/0284744 A1 Oct. 8, 2015

Related U.S. Application Data

(63) Continuation of application No. PCT/US2014/052386, filed on Aug. 22, 2014.

(60) Provisional application No. 61/868,582, filed on Aug. 22, 2013, provisional application No. 61/948,441, filed on Mar. 5, 2014.

(51) Int. Cl.
| | |
|---|---|
| C12N 1/20 | (2006.01) |
| C12N 15/74 | (2006.01) |
| C12P 15/00 | (2006.01) |
| C12P 7/44 | (2006.01) |
| C12P 5/00 | (2006.01) |
| C07H 21/04 | (2006.01) |
| C12N 9/88 | (2006.01) |
| C07K 14/195 | (2006.01) |
| C07K 14/245 | (2006.01) |

(52) U.S. Cl.
CPC .............. *C12P 5/007* (2013.01); *C07K 14/195* (2013.01); *C07K 14/245* (2013.01); *C12N 9/88* (2013.01); *C12P 5/002* (2013.01); *C12P 7/44* (2013.01); *C12P 15/00* (2013.01); *C12Y 402/03* (2013.01); *Y02E 50/343* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,533,487 A | 8/1985 | Jones | |
| 2011/0294183 A1* | 12/2011 | Dunlop et al. | 435/170 |
| 2012/0064622 A1* | 3/2012 | Fischer et al. | 435/348 |
| 2012/0205284 A1 | 8/2012 | Harvey et al. | |
| 2013/0078690 A1 | 3/2013 | Reed | |
| 2013/0089899 A1 | 4/2013 | Kurek et al. | |
| 2013/0130345 A1 | 5/2013 | Thai et al. | |
| 2013/0149755 A1 | 6/2013 | Reed et al. | |
| 2013/0189763 A1 | 7/2013 | Dalla-Betta | |
| 2014/0273112 A1 | 9/2014 | Reed et al. | |
| 2015/0017694 A1 | 1/2015 | Kurek et al. | |
| 2015/0140640 A1 | 5/2015 | Reed et al. | |

FOREIGN PATENT DOCUMENTS

| | | |
|---|---|---|
| WO | WO2007139924 A2 | 12/2007 |
| WO | WO2010078378 A2 | 7/2010 |
| WO | WO2011056183 A1 | 5/2011 |
| WO | WO2011139804 A2 | 11/2011 |
| WO | WO2013082309 A1 | 6/2013 |
| WO | WO2013090769 A2 | 6/2013 |
| WO | WO2013148348 A1 | 10/2013 |
| WO | WO2014145194 A2 | 9/2014 |
| WO | WO2015027209 A3 | 2/2015 |

OTHER PUBLICATIONS

Jansson, C., Metabolic Engineering of Cyanobacteria for Direct Conversion of CO2 to Hydrocarbon Biofuels, Progress in Botany, Jan. 2012; 73:81-93.
Altschul, S., et al., Gapped BLAST and PSI-BLAST: a new generation of protein database search programs, Nuc. Acids Res., 1997; 25:3389-3402.
Altschul, S., et al., Basic Local Alignment Search Tool, J. Mol. Biol., 1990; 215:403-410.
Henikoff, S., et al., Amino Acid Substitution Matrices From Protein Blocks, Proc. Natl. Acad. Sci. USA, 1992; 89: 10915-10919.
Karlin, S., et al., Applications and Sequences for Multiple High-scoring Segments in Molecular Sequences, Proc. Natl. Acad. Sci. USA, 1993; 90, 5873-5777.
Higgins, D., et al., CLUSTAL: A Package for Performing Multiple Sequence Alignment on a Microcomputer Gene, Jan. 1998; 73:237-244.
Pearson, W., et al., Improved Tools for Biological Sequence Comparison, Proc. Natl. Acad. Sci., 1988; 85:2444-2448.
Dunlop, M., et al., Engineering Microbial Biofuel Tolerance and Export Using Efflux Pumps, Molecular Systems Biology, 2011; 7(487).
Harvey, B., et al., High-Density Renewable Fuels Based on the Selective Dimerization of Pinenes ,Energy Fuels, 2010; 24(1):267-273.
Meylemans, H., et al., Efficient Conversion of Pure and Mixed Terpene Feedstocks to High Density Fuels, Fuel, Jul. 2012, 97:560-568.
Poole, K, Efflux-mediated Antimicrobial Resistance, J Antimicrob Chemoth, 2005; 56:20-51.
Eda, S, et al., An Elegant Means of Self-protection in Gram-negative Bacteria by Recognizing and Extruding Xenobiotics from the Periplasmic Space, J Biol Chem., 2003; 278(4):2085-2088.

(Continued)

Primary Examiner — Iqbal H Chowdhury
(74) Attorney, Agent, or Firm — Jill A. Jacobson

(57) ABSTRACT

Engineered microorganisms are provided that convert gaseous substrates, such as producer gas, into limonene. In some embodiments, limonene is pumped out of the cell via an efflux pump. In some embodiments, limonene, produced as described herein, is converted through catalytic dimerization into jet fuel. Producer gas used in the processes described herein for production of limonene may be derived from sources that include gasification of waste feedstock and/or biomass residue, waste gas from industrial processes, or natural gas, biogas, or landfill gas.

27 Claims, 11 Drawing Sheets

(56) References Cited

OTHER PUBLICATIONS

Elkins, C., et al., Substrate Specificity of the RND-Type Multidrug Efflux Pumps AcrB and AcrD of *Escherichia coli* is Determined Predominately by Two Large Periplasmic Loops, J. Bacteriol., Dec. 2002; 184(23):6490-6498.

Alonso-Gutierrez, J., et al., Metabolic Engineering of *Escherichia coli* for Limonene and Perillyl Acolhol Production, Metabolic Engineering, Sep. 2013; 19:33-41.

Bentley, F., et al., Pardigm of Monoterpene (B-phellandrene) Hydrocarbons Production via Photosynthesis in Cyanobacteria, BioEngergy Research, 2013; 6(3): 917-929.

Engler, C., et al. Golden Gate Cloning, Methods Mol. Biol., 2014; 1116:119-131.

Bi, C. et al., Development of a Broad-host Synthetic Biology Toolbox for Ralstonia Eutropha and its Application to Engineering Hydrocarbon Biofuel Production, Microb. Cell Fact., 2013; 12:107.

Engler, C., et al., Golden Gate Shuffling: a One-pot DNA Shuffling Method Based on Type IIs Restriction Enzymes, PLoS One, 2009; 4(5):e5553.

Kovach, M., et al., Four new derivatives of the broad-host-range cloning vector pBBR1MCS, carrying different antibiotic-resistance cassettes, Gene, 1995; 166:175-176.

Poehlein, A, et al. Complete Genome Sequence of the Type Strain Cupriavidus necator N-1, J. Bacteriol., Sep. 2011; 193(18):5017.

NCBI Reference Sequence: YP_004685497.1 "multidrug resistance protein MexB [Cupriavidus neacator N-1]" Jun. 27, 2013, [recovered from the internet Jun. 11, 2014].

NCBI Reference Sequence: YP_004687455.1 acriflavine resistance protein B [Cupriavidus neator N-1]: Jun. 27, 2013, [recovered from the internet Jun. 11, 2014].

NCBI Reference Sequence: YP_004687080.1 "cation/multidrug efflux pump [Cupriavidus neactor N-1]" Jun. 27, 2013, [recovered from the internet Jun. 11, 2014].

Rittman, B.E. and McCarty, P.L., Chapter 2: Stoichiometry and Bacterial Energetics, in Environmental biotechnology: principles and applications, McGraw-Hill, 2001.

Botheju, D. and Bakke, R., Oxygen Effects in Anaerobic Digestion—A Review, The Open Waste Management Journal, 4:1-19, 2011.

Aleeva, S., et al., Quantitative Assessment of Oxygen Availability: Perceived Aerobiosis and Its Effect on Flux Distribution in the Respiratory Chain of *Escherichia coli*, 184(5):1402-1406, 2002.

Sandoval-Basurto, E., et al., Culture of *Escherichia coli* Under Dissolved Oxygen Gradients Simulated in a Two-Compartment Scale-Down System: Metabolic Response and Production of Recombinant Protein.

\* cited by examiner

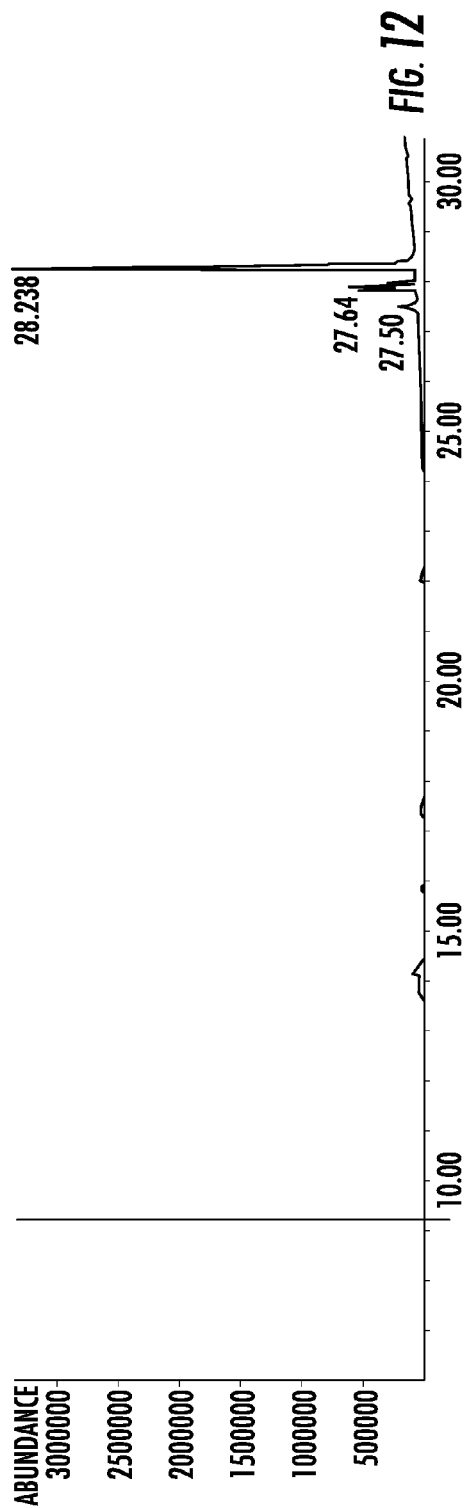
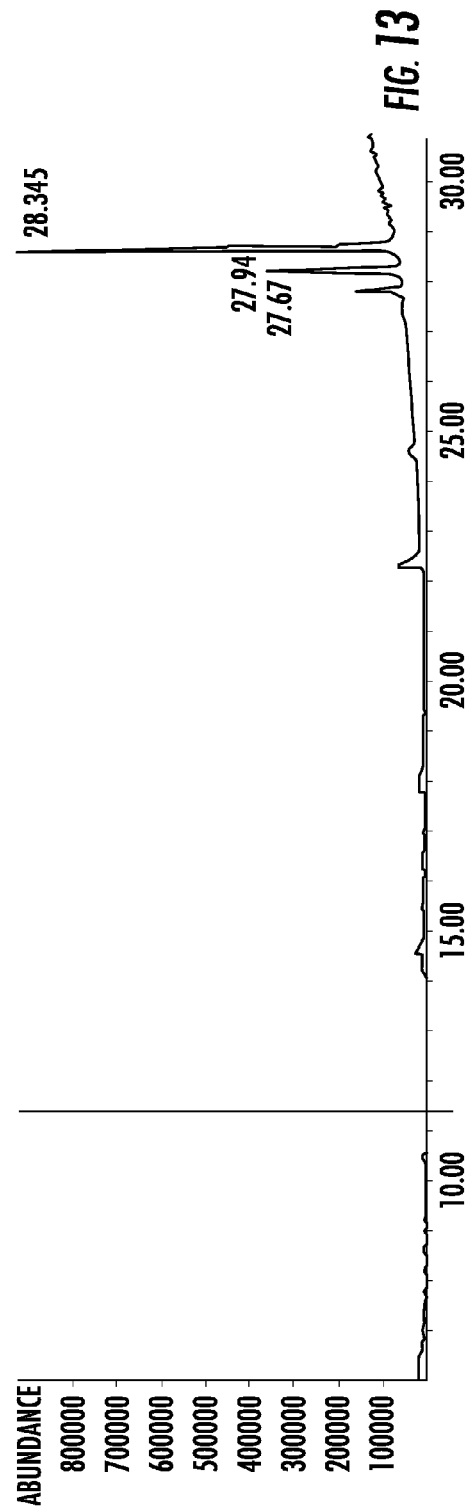

US 9,506,086 B2

MICROORGANISMS FOR BIOSYNTHESIS OF LIMONENE ON GASEOUS SUBSTRATES

CROSS-REFERENCE TO RELATED APPLICATIONS

This application is a continuation under 35 U.S.C. 365(c) of PCT Application No. PCT/US14/52386, filed on Aug. 22, 2014, which claims the benefit of U.S. Provisional Application No. 61/868,582, filed on Aug. 22, 2013, and 61/948,441, filed on Mar. 5, 2014, both of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 29, 2015, is named 164185.P002U2_SL.txt and is 3,858 bytes in size.

FIELD OF THE INVENTION

The inventive subject matter relates to the biosynthetic production of terpenes, such as limonene, in a microbial system, using a gaseous substrate such as producer gas or $H_2$ and $CO_2$ gas mixtures, as a carbon and energy source. The invention also relates to the extraction of terpenes, such as limonene from microbial cells, or the recovery of terpenes that are excreted from microbial cells via active transport, for example, via efflux pumps or via passive transport.

BACKGROUND

Limonene is a 10-carbon monoterpene with the formula $C_{10}H_{16}$ that is an isomer of Tetrahydrodiclopentadiene, also known as JP-10 jet fuel, a high energy density and expensive fuel. When dimerized, limonene can be converted into a high energy density (HED) jet fuel with similar properties to JP-10 jet fuel.

Limonene is obtained as a byproduct of citrus processing from rind of citrus fruits. The major barrier for widespread application of limonene in a variety of products has largely been the relatively high price, high pricing volatility, and supply side uncertainty associated with citrus limonene, which is the largest source of the compound. Intrinsically limonene is a very versatile and useful intermediate chemical and fuel. However, in practice its utilization has been limited due to its high per unit price and limited availability. Due to limited volumetric availability of terpenes such as limonene, which are mostly plant-derived and produced in small quantities, the approach of using limonene and other terpenes for producing significant volumes of jet fuel has not been feasible and hence has not been pursued by the industry to date.

The need remains for a way to produce high volumes of terpenes, such as limonene, from feedstocks that are readily available, abundant, and cheap.

There also is a need to break the bottleneck associated with biologically producing economically competitive replacements for petroleum derived fuels and chemicals on a very large scale. There is a need for bioprocesses with compact, vertical scaling as opposed to traditional biofuel operations that scale horizontally and are land intensive. In this way, the food versus fuel question and conflicts over land use and disruption of natural habitats can be more readily avoided. There is a need for monoterpene sources with predictably higher margins and greater supply security.

BRIEF SUMMARY OF THE INVENTION

In one aspect, an engineered microorganism is provided that is capable of converting a gaseous substrate such as producer gas or another gas mixture that contains $H_2$ and $CO_2$, and/or CO, and/or CH4 into limonene. The gaseous substrate is used by the microorganism as a carbon and/or energy source. In some embodiments, microorganisms that are capable of growing on a gaseous substrate are transformed with a polynucleotide that encodes a gene that is required for biosynthesis of limonene, for example, limonene synthase. In some embodiments, limonene is recovered from the microbial cells or from a microbial growth medium. In some embodiments limonene is then converted through catalytic dimerization, for example, with Nafion SAC-13 or MMKT-K10, into High Energy Density Jet Fuel. Producer gas, which may be used in the microbial growth processes described herein, may come from sources that include gasification of waste feedstock and/or biomass residue feedstock, or waste gas from industrial processes or steam reforming of natural gas or biogas.

In one aspect, a non-naturally occurring microorganism is provided that is capable of growing on a gaseous substrate as a carbon and/or energy source, and wherein the microorganism includes at least one exogenous nucleic acid encoding a limonene synthase enzyme. For example, the at least one exogenous nucleic acid may encode a (4S) limonene synthase enzyme and/or a (4R) limonene synthase enzyme. In some embodiments, the microorganism is a bacterial cell. For example, in some embodiments, the bacterial cell is a *Cupriavidus* sp. or *Ralstonia* sp., for example, but not limited to, *Cupriavidus necator*.

In some embodiments, the gaseous substrate includes $CO_2$ as a carbon source. In some embodiments, the gaseous substrate includes $H_2$ and/or $O_2$ as an energy source. In some embodiments, the gaseous substrate includes producer gas or syngas. In some embodiments, the gaseous substrate includes a mixture of gases, comprising $H_2$ and/or $CO_2$ and/or CO.

In some embodiments, the microorganism produces limonene when cultured in the presence of the gas substrate under conditions suitable for growth of the microorganism and production of bioproducts.

In some embodiments, the microorganism includes one or more exogenous nucleic acid encoding an efflux pump. In some embodiments, the microorganism that expresses an exogenous efflux pump produces limonene, wherein a greater amount of limonene is transported out of the microorganism and into a growth medium in which the microorganism is cultured than an equivalent microorganism that does not express the efflux transport protein. In some embodiments, the exogenous nucleic acid encoding an efflux pump encodes *A. borkumensis* YP_692684 protein. In some embodiments, the exogenous nucleic acid encoding an efflux pump encodes *E. coli* AcrB protein.

In some embodiments, the microorganism has the ability to overexpress one or more native efflux pump. In some embodiments, the microorganism (for example, a *Cupriavidus* species, such as *Cupriavidus necator*) overexpresses the native efflux pump YP_004685497. In some embodiments, the microorganism (for example, a *Cupriavidus* species, such as *Cupriavidus necator*) overexpresses the native efflux pump YP_004687455. In some embodiments, the microorganism (for example, a *Cupriavidus* species, such as *Cupria-* vidus necator) overexpresses the native efflux pump YP_004687080. In some embodiments, the microorganism that overexpresses a native efflux pump produces limonene, wherein a greater amount of limonene is transported out of the microorganism and into a growth medium in which the microorganism is cultured than an equivalent microorganism that does not have the ability to overexpress the native efflux pump.

In some embodiments, limonene synthase is encoded by a coding sequence in the non-naturally occurring microorganism that is carried on a broad-host-range plasmid. In some embodiments, the limonene synthase coding sequence is under the control of a non-native inducible promoter. In some embodiments, the inducible promoter is derived from the E. coli ara operon.

In some embodiments, production of limonene by a microorganism as described herein is accomplished by the addition of a single-step reaction downstream of geranyl pyrophosphate (GPP) in the MEP pathway, catalyzed by limonene synthase from Citrus unshiu (Uniprot Q6F5H3). In some embodiments, the coding sequence (CDS) of the limonene synthase (LS) gene from Citrus unshiu (Uniprot Q6F5H3) is codon optimized for expression in a microorganism of as described herein, for example, but not limited to a Ralstonia or Cupriavidus species, for example, Cupriavidus necator.

In another aspect, methods are provided for producing limonene using an engineered microorganism as described herein that is capable of growing on a gaseous substrate as a carbon and/or energy source, and that includes at least one exogenous nucleic acid encoding a limonene synthase enzyme. In some embodiments, a non-naturally occurring microorganism as described herein is cultured in a bioreactor that includes a gaseous substrate and a culture medium (e.g., a liquid growth medium) that includes other nutrients for growth and bioproduct production, under conditions that are suitable for growth of the microorganism and production of limonene, wherein the microorganism produces limonene.

In some embodiments, the gaseous substrate in the bioreactor includes $H_2$ and/or $CO_2$. In some embodiments, the gaseous substrate is producer gas or syngas. In some embodiments, the gaseous substrate is derived from municipal solid waste, black liquor, agricultural waste, wood waste, stranded natural gas, biogas, sour gas, methane hydrates, tires, pet coke, sewage, manure, straw, lignocellulosic energy crops, lignin, crop residues, bagasse, saw dust, forestry residue, food waste, waste carpet, waste plastic, landfill gas, and/or lignocellulosic biomass.

In some embodiments, limonene is recovered from the culture medium. In some embodiments, limonene is recovered from the surface of the culture medium at the interface between the liquid and gas phases in the bioreactor. In some embodiments, the culture medium is a biphasic liquid medium that includes an aqueous phase and an organic phase, and limonene is recovered in the organic phase. In some embodiments, the organic phase comprises dodecane.

In another aspect, limonene that is produced by an engineered microorganism using a gaseous substrate as described herein is dimerized to produce jet fuel. For example, Nafion SAC-13 and/or MMKT-K10 may be used for dimerization of limonene.

In another aspect, limonene that is produced by an engineered microorganism using a gaseous substrate as described herein is converted to terephthalic acid.

In another aspect, microorganisms and methods for producing squalene are provided. In some embodiments, a non-naturally occurring microorganism is provided that is capable of growing on a gaseous substrate as a carbon and/or energy source, wherein the microorganism includes at least one exogenous nucleic acid, and wherein said microorganism biosynthesizes squalene. In some embodiments, the non-naturally occurring microorganism is a Cupriavidus sp. or Ralstonia sp. In some embodiments, the microorganism is Cupriavidus necator. In some embodiments, a method is provided for producing squalene in non-naturally occurring microorganism as described herein that is capable of growing on a gaseous substrate as a carbon and/or energy source, that includes at least one exogenous nucleic acid, and that biosynthesizes squalene, including culturing the non-naturally occurring microorganism in a bioreactor that includes a gaseous substrate and a culture medium (e.g., a liquid growth medium) that includes other nutrients for growth and bioproduct production, under conditions that are suitable for growth of the microorganism and production of squalene, wherein the microorganism produces squalene.

Various objects, features, aspects, and advantages of the present invention will become more apparent from the following detailed description of preferred embodiments of the invention, along with the accompanying drawings in which like numerals represent like components

BRIEF DESCRIPTION OF THE DRAWINGS

FIG. 12: First replicate squalene GC peak at 28.338, as described in Example 4.

FIG. 13: Second replicate squalene GC peak at 28.345, as described in Example 4.

DETAILED DESCRIPTION

Provided herein are methods and systems for biosynthetic production of terpenes, such as limonene. Engineered microorganisms are provided that produce terpenes, such as limonene, on a gaseous substrate, including, but not limited to producer gas, syngas, tail gas, knallgas, and gas mixtures containing H2 and CO2, and/or CO and/or CH4. The gaseous substrate may serve as a carbon and energy source and a source of electron donors and/or electron acceptors for growth of the microorganisms and biosynthesis of bioproducts.

Figures 1, 2:
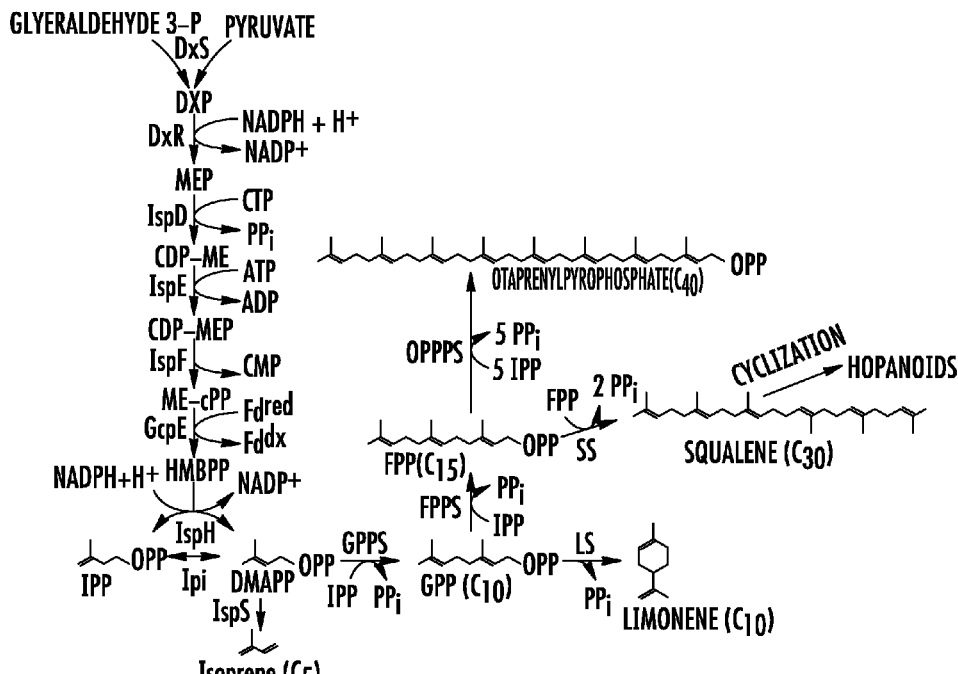
FIG. 1: The methyl-erythritol-4-phosphate (MEP) pathway as it occurs in plant and algal chloroplasts and in cyanobacteria and other bacteria. Monoterpenes are common in plants and algae but are not usually produced in bacteria. Formation of limonene is indicated. (Jansson (2012) Progress in Botany 73:81)
FIG. 2: In some embodiments the engineered strain carries efflux pumps. Examples of efflux pumps that may be used in non-limiting embodiments of the current invention include efflux pumps with high homology to efflux pumps patented by the Joint BioEnergy Institute (JBEI); patent number U.S. Ser. No. 13/115,925 Dunlop et al. Example homologies were calculated using NCBI BLAST (Altschul S F et al (1997) Nucleic Acids Res 25: 3389-3402)
Figure 3:
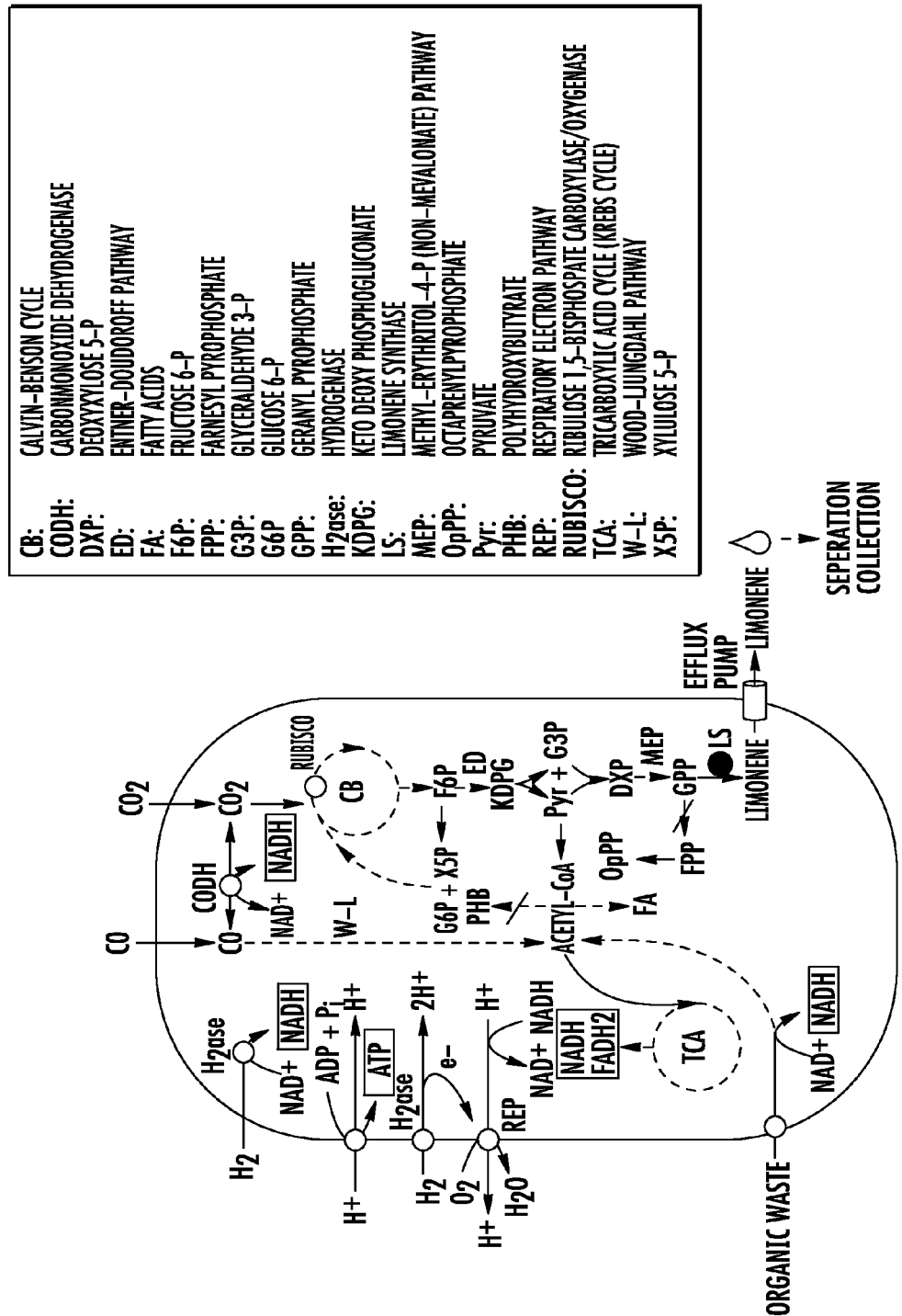
FIG. 3: Schematic of central metabolism in the strain in a non-limiting embodiment of the current invention. Major pools of reducing power (NADH, $FADH_2$) and ATP recruited by the Calvin-Benson cycle (CB) and non-CB anabolism are boxed. In chemoautotrophic (lithoautotrophic) growth mode, the strain utilizes $H_2$ and/or CO as energy source(s) and electron donor(s) and $CO_2$ and/or CO as carbon source(s). Installation of the Limonene synthase (LS) and efflux pump for biosynthesis and facilitated export of limonene is shown. Pathways slated for suppression in certain embodiments as a means to enhance carbon flux toward limonene biosynthesis are indicated by bars.
Figure 4:
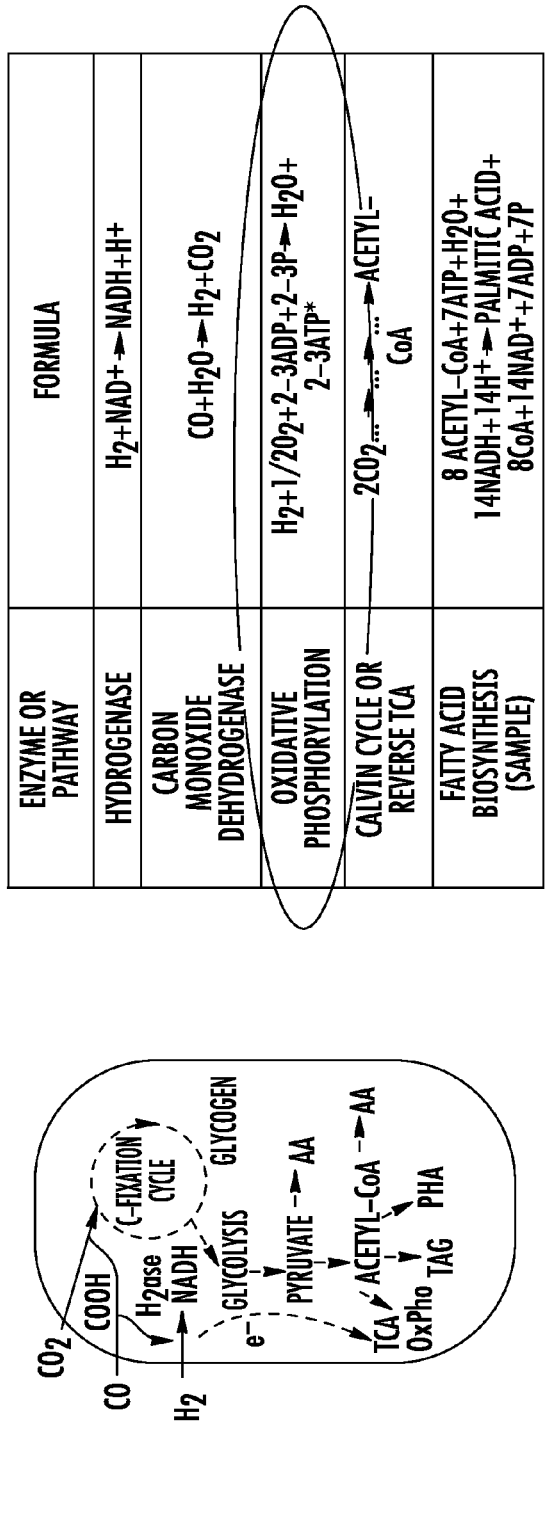
FIG. 4: Pathways of knallgas microorganisms.

In some embodiments, the microorganisms disclosed herein are recombinantly engineered to express one or more enzymes for biosynthetic production of limonene, for example, limonene synthase. In some embodiments, substrates or intermediates are diverted to limonene synthesis in the microbial cells, for example, Geranyl pyrophosphate (GPP). In some non-limiting embodiments some fraction of carbon flux along the methyl-erythritol-4-phosphate pathway is directed into the biosynthesis of limonene. In some embodiments the action of limonene synthase (LS) in the production of limonene is as illustrated in FIG. 1.

In some embodiments, the microorganisms are engineered to express one or more transport protein(s) for secretion of terpenes, e.g., limonene, out of the cells. In some non-limiting embodiments the transport proteins include but are not limited to *E. coli* AcrB. In some non-limiting embodiments the transport proteins include but are not limited to the Ab pump encoded by the YP_692684 gene in *Alcanivorax borkumensis*. In some embodiments the transport proteins include but are not limited to those encoded by one or more of the following *Cupriavidus necator* genes: YP_004685497, YP_004687455, YP_004687080.

In some embodiments, the recombinant microorganisms herein may be grown in a biphasic growth medium that includes an aqueous growth medium and an organic solvent phase in which the terpene, e.g., limonene, product is soluble. In some embodiments, the solvent phase draws off the terpene, e.g., limonene, product, keeping concentration low in the aqueous growth medium and reducing product toxicity to the microorganisms.

Unless defined otherwise herein, all technical and scientific terms used herein have the same meaning as commonly understood by one of ordinary skill in the art to which this invention belongs. Singleton, et al., Dictionary of *Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

DEFINITIONS

"A," "an" and "the" include plural references unless the context clearly dictates "Titer" refers to amount of a substance produced by a microorganism per unit volume in a microbial fermentation process. For example, limonene titer may be expressed as grams of limonene produced per liter of solution.

"Yield" refers to amount of a product produced from a feed material (for example, sugar) relative to the total amount that of the substance that would be produced if all of the feed substance were converted to product. For example, limonene yield may be expressed as % of limonene produced relative to a theoretical yield if 100% of the feed substance were converted to limonene.

"Productivity" refers to the amount of a substance produced by a microorganism per unit volume per unit time in a microbial fermentation process. For example, limonene productivity may be expressed as grams of limonene produced per liter of solution per hour.

"Wild-type" refers to a microorganism as it occurs in nature.

As used herein, the term "polynucleotide" refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides, which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide," "nucleic acid," and "oligonucleotide" are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR.sub.2 ("amidate"), P(O)R, P(O)OR', CO or CH.sub.2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, the term "expression" refers to the process by which a polypeptide is produced based on the nucleic acid sequence of a gene. The process includes both transcription and translation.

As used herein, "expression vector" refers to a DNA construct containing a DNA coding sequence (e.g., gene sequence) that is operably linked to one or more suitable control sequence(s) capable of effecting expression of the coding sequence in a host. Such control sequences include a promoter to effect transcription, an optional operator sequence to control such transcription, a sequence encoding suitable mRNA ribosome binding sites, and sequences that control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the invention is intended to include such other forms of expression vectors that serve equivalent functions and which are, or become, known in the art.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

The term "operably linked" refers to a juxtaposition or arrangement of specified elements that allows them to perform in concert to bring about an effect. For example, a promoter is operably linked to a coding sequence if it controls the transcription of the coding sequence.

"Under transcriptional control" is a term well understood in the art that indicates that transcription of a polynucleotide sequence depends on its being operably linked to an element that contributes to the initiation of, or promotes transcription.

"Under translational control" is a term well understood in the art that indicates a regulatory process that occurs after mRNA has been formed.

A "gene" refers to a DNA segment that is involved in producing a polypeptide and includes regions preceding and following the coding regions as well as intervening sequences (introns) between individual coding segments (exons).

As used herein, the term "host cell" refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a protein, which facilitates the secretion of the mature form of the protein from the cell. The mature form of the extracellular protein lacks the signal sequence, which is cleaved off during the secretion process.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "derived from" encompasses the terms "originated from," "obtained from," "obtainable from," "isolated from," and "created from," and generally indicates that one specified material finds its origin in another specified material or has features that can be described with reference to the another specified material.

The term "culturing" refers to growing a population of cells, e.g., microbial cells, under suitable conditions for growth, in a liquid or solid medium.

The term "heterologous," with reference to a polynucleotide or protein, refers to a polynucleotide or protein that does not naturally occur in a specified cell, e.g., a host cell. It is intended that the term encompass proteins that are encoded by naturally occurring genes, mutated genes, and/or synthetic genes. In contrast, the term "homologous," with reference to a polynucleotide or protein, refers to a polynucleotide or protein that occurs naturally in the cell.

The term "introduced," in the context of inserting a nucleic acid sequence into a cell, includes "transfection," "transformation," or "transduction" and refers to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed.

"Transfection" or "transformation" refers to the insertion of an exogenous polynucleotide into a host cell. The exogenous polynucleotide may be maintained as a non-integrated vector, for example, a plasmid, or alternatively, may be integrated into the host cell genome. The term "transfecting" or "transfection" is intended to encompass all conventional techniques for introducing nucleic acid into host cells. Examples of transfection techniques include, but are not limited to, calcium phosphate precipitation, DEAE-dextran-mediated transfection, lipofection, electroporation, and microinjection.

As used herein, the terms "transformed," "stably transformed," and "transgenic" refer to a cell that has a non-native (e.g., heterologous) nucleic acid sequence integrated into its genome or as an episomal plasmid that is maintained through multiple generations.

The terms "recovered," "isolated," "purified," and "separated" as used herein refer to a material (e.g., a protein, nucleic acid, or cell) that is removed from at least one component with which it is naturally associated. For example, these terms may refer to a material that is substantially or essentially free from components which normally accompany it as found in its native state, such as, for example, an intact biological system.

A "signal sequence" (also termed "presequence," "signal peptide," "leader sequence," or "leader peptide") refers to a sequence of amino acids at the amino terminus of a nascent polypeptide that targets the polypeptide to the secretory pathway and is cleaved from the nascent polypeptide once it is translocated in the endoplasmic reticulum membrane.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins.

The phrases "substantially similar" and "substantially identical" in the context of at least two nucleic acids or polypeptides typically means that a polynucleotide or polypeptide comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

"Chemoautotrophic" refers to organisms that obtain energy by the oxidation of chemical electron donors by chemical electron acceptors and synthesize all the organic compounds needed by the organism to live and grow from carbon dioxide.

"Lithoautotrophic" refers to a specific type of chemoautotrophy where the organism utilizes the oxidation of inorganic chemical electron donors by inorganic chemical electron acceptors as an energy source.

The term "knallgas" refers to the mixture of molecular hydrogen and oxygen gas. A "knallgas microorganism" is a microbe that can use hydrogen as an electron donor and oxygen as an electron acceptor in the generation of intracellular energy carriers such as Adenosine-5'-triphosphate (ATP). The terms "oxyhydrogen" and "oxyhydrogen microorganism" can be used synonymously with "knallgas" and "knallgas microorganism" respectively.

"Heterotrophic" refers to organisms that cannot synthesize all the organic compounds needed by the organism to live and grow from carbon dioxide and which must utilize organic compounds for growth.

"Sulfur-oxidizer" refers to microorganisms that utilize reduced sulfur containing compounds including but not limited to $H_2S$ as electron donors for the production of intracellular reducing equivalents and/or in respiration.

"Hydrogen-oxidizer" refers to microorganisms that utilize reduced $H_2$ as an electron donor for the production of intracellular reducing equivalents and/or in respiration.

"Iron-oxidizer" refers to microorganisms that utilize reduced iron containing compounds including but not limited to ferrous iron (Fe(II)) as electron donors for the production of intracellular reducing equivalents and/or in respiration.

"Acetogen" refers to microorganisms that generate acetate and/or other short chain organic acids up to $C_4$ chain length as a product of anaerobic respiration.

"Methanogen" refers to a microorganism that generates methane as a product of anaerobic respiration.

"Methylotroph" refers to microorganisms that can use reduced one-carbon compounds, such as but not limited to methanol or methane, as a carbon source and/or as an electron donor for their growth.

"Extremophile" refers to microorganisms that thrive in physically or geochemically extreme conditions (e.g. high or low temperature, pH, or high salinity) compared to conditions on the surface of the Earth or the ocean typically tolerated by most life forms.

"Thermophile" refers to a type of extremophile that thrives at relatively high temperatures for life, between 45 and 122° C.

"Hyperthermophile" refers to a type of extremophile that thrives in extremely hot environments for life, from 60° C. (140° F.) upwards.

"Acidophile" refers to a type of extremophile that thrives under highly acidic conditions (usually at pH 2.0 or below).

"Halophile" refers to a type of extremophile that thrives in environments with very high concentrations of salt.

"Psychrophile" refers to a type of extremophile capable of growth and reproduction in cold temperatures, ranging from 10° C. and below.

"Producer gas" refers to gas mixture containing various proportions of $H_2$, CO, and $CO_2$, and having heat value typically ranging between one half and one tenth that of natural gas per unit volume under standard conditions. Producer gas can be generated various ways from a variety of feedstocks including gasification, steam reforming, or autoreforming of carbon-based feedstocks. In addition to $H_2$, CO, and $CO_2$, producer gases can contain other constituents including but not limited to methane, hydrogen sulfide, condensable gases, tars, and ash depending upon the generation process and feedstock. The proportion of $N_2$ in the mixture can be high or low depending upon if air is used as an oxidant in the reactor or not and if the heat for the reaction is provided by direct combustion or through indirect heat exchange.

"Syngas" or "Synthesis gas" refers to a type of gas mixture, which like producer gas contains $H_2$ and CO, but which has been more specifically tailored in terms of $H_2$ and CO content and ratio and levels of impurities for the synthesis of a particular type of chemical product, such as but not limited to methanol or fischer-tropsch diesel.

"Carbon source" refers to the types of molecules from which a microorganism derives the carbon needed for organic biosynthesis.

"Energy source" refers to either the electron donor that is oxidized by oxygen in aerobic respiration or the combination of electron donor that is oxidized and electron acceptor that is reduced in anaerobic respiration.

"Efflux pump" refers to cellular pumps involved in the flowing out of a particular substance or particle from the intracellular to the extracellular space.

"Biphasic growth environment" refers to a growth environment containing two immiscible liquid phases.

The term "gasification" refers to a generally high temperature process that converts carbon-based materials into a mixture of gases including hydrogen, carbon monoxide, and carbon dioxide called syngas or producer gas. The process generally involves partial combustion and/or the application of externally generated heat along with the controlled addition of oxygen and/or steam such that insufficient oxygen is present for complete combustion of the carbon-based material.

The term "hydrocarbon" refers to a molecule composed exclusively of carbon and hydrogen atoms with the carbons bonded covalently in a branched, cyclic, linear, or partially cyclic chain and with hydrogen atoms covalently bonded to the carbons such that the chemical octet rule for the carbons is generally satisfied. In some hydrocarbons there may occur some number of double or triple bonds between adjacent carbon atoms in the chain. Thus, the label hydrocarbon subsumes branched, cyclic, linear, branched, or partially cyclic alkanes (also called paraffins), alkenes (also called olefins), and alkynes. The structure of hydrocarbon molecules range from the smallest, methane ($CH_4$), a primary component of natural gas, to high molecular weight complex molecules including asphaltenes present in bitumens crude oil, and petroleum. Other examples include dodecane ($C_{12}$), hexadecane ($C_{16}$), or octadecane ($C_{18}$) etc. Hydrocarbons of the present invention may be in gaseous, liquid, or solid phases, either as singly or in multiply coexisting phases.

The term "hydrophobic" refers to matter that has low solubility in water and greater solubility in a hydrophobic phase than in an aqueous phase.

The terms "microorganism" and "microbe" mean microscopic single celled life forms.

The term "molecule" means any distinct or distinguishable structural unit of matter comprising one or more atoms, and includes for example hydrocarbons, lipids, polypeptides and polynucleotides.

The term "organic compound" refers to any gaseous, liquid, or solid chemical compounds which contain carbon atoms with the following exceptions that are considered inorganic: carbides, carbonates, simple oxides of carbon, cyanides, and allotropes of pure carbon such as diamond and graphite.

Limonene and Other Monoterpenes

Limonene is a 10-carbon monoterpene (FIG. 1) with high energy density. Biologically produced limonene can serve as drop-in bio-gasoline, while dimerization of the molecule will generate jet-fuel and biological diesel products with excellent metrics of combustion. The meritorious characteristics of limonene, and monoterpenes more generally, as fuels are recognized, and include for jet fuel, higher volumetric energy density than JP-8 or Jet-A, rivaling the high price specialty jet fuel JP-10. (Engineering microbial biofuel tolerance and export using efflux pumps Molecular Systems Biology, Vol. 7, No. 1. (10 May 2011), doi:10.1038/msb.2011.21 by Mary Dunlop, Zain Y. Dossani, Heather L. Szmidt, et al.; High-Density Renewable Fuels Based on the Selective Dimerization of Pinenes Energy Fuels, Vol. 24, No. 1. (13 Nov. 2009), pp. 267-273, doi:10.1021/ef900799c by Benjamin G. Harvey, Michael E. Wright, Roxanne L. Quintana; Efficient conversion of pure and mixed terpene feedstocks to high density fuels Fuel, Vol. 97 (July 2012), pp. 560-568, doi:10.1016/j.fuel.2012.01.062 by Heather A. Meylemans, Roxanne L. Quintana, Benjamin G. Harvey) Higher volumetric energy density translates to increased flight range on a tank of fuel.

Limonene is a molecule with a number of meritorious characteristics, in addition to its potential as a high energy density liquid fuel, including: multiple current and potential uses in specialty and commodity chemical applications, both as a finished chemical and as a chemical feedstock; very low human toxicity; and is a very environmentally benign type of hydrocarbon.

Limonene is naturally found in essential oils of citrus, and gives the fruit its scent. Current industrial production of limonene is restricted due to its source—direct extraction of dilute amounts contained in citrus peels. Consequently limonene prices can be quite high due to its inefficient production—recently prices have been around $7/kg—thus limiting it current uses.

Monoterpenes are part of the largest and most diverse group of naturally occurring organic compounds referred to as isoprenoids or terpenoids. Limonene and monoterpenes generally have significant commercial potential, as a fuel feedstock, and are useful in direct applications similar to other hydrocarbons, e.g. in gasoline. In addition, dimerization of limonene units may generate second-order fuel molecules, suitable for use as supplements of jet fuel and biodiesel. Physicochemical properties of limonene and its derivatives are consistent with use of this molecule as renewable fuel feedstock. (Chemical Dictionary Online, http://www.chemicaldictionary.org/dic/D/D-Limonene_332.html; Standard Thermodynamic Properties of Chemical Substances, http://courses.chem.indiana.edu/c360/documents/thermodynamicdata.pdf.)

Limonene has an energy density of 37.8 MJ $L^{-1}$ and thus has an energy density well above ethanol (energy density ≥26.8 MJ $L^{-1}$) (14). With a melting point (Tm)=$-74°$ C., boiling point (Tb)=$+175.5°$ C., and a heat of combustion ($\Delta H_c°$) equal to 6,167 kJ $mol^{-1}$, limonene is well suited for use as fuel in a variety of climatic conditions.

In some embodiments the limonene produced in the present invention is used as a replacement for gasoline fuel. In some embodiments it is dimerized to produce a jet fuel or a diesel fuel. In some embodiments limonene spontaneously separates from the cells and accumulates as "floater molecules" on the surface of the liquid medium, alleviating the need for costly and laborious culture dewatering and product extraction. In some embodiments secretion of the terpene molecules will physically and kinetically sequester the molecules from cellular metabolism, continuously pushing the synthesis reaction forward and preventing terpene products from accumulating to toxicity levels in the cell.

There are two known isoprenoid pathways: the methylerythritol-4-phosphate (MEP) pathway also known as the non-mevalonate pathway and the Mevalonic acid pathway (MVA). In both types of isoprenoid pathways geranyl pyrophosphate (GPP) is a metabolic intermediate. In some embodiments of the present invention either the MEP or MVA pathway for isoprenoid biosynthesis is used for the production of limonene by adding a single-step reaction downstream of GPP catalyzed by limonene synthase. In some embodiments the limonene synthase is a (4S)-limonene synthase. In some other embodiments the limonene synthase is a (4R)-limonene synthase. In some embodiments the carbon flux towards limonene biosynthesis is increased by removing anabolic reactions toward glycogen and other storage compounds.

In certain non-limiting embodiments the terpene produced by non-naturally occurring microorganisms as described herein is Squalene. In certain non-limiting embodiments, gaseous feedstock is converted to organic compounds including Squalene by microorganisms as described herein. In certain non-limiting embodiments the microorganism producing terpene compounds including Squalene is *Cupriavidus* sp. or *Ralstonia* sp. In certain non-limiting embodiments the microorganism producing organic terpene including Squalene is *Cupriavidus necator*. In certain non-limiting embodiments the microorganism producing terpene compounds including Squalene is *Cupriavidus necator* DSM 531.

Production of Monoterpenes from Gaseous Energy and Carbon Substrates

Engineered microorganisms are provided that are capable of converting producer gas or a gas mixture containing H2 and/or CO and/or CO2 and/or CH4 into limonene. In some embodiments the limonene is then converted through catalytic dimerization with Nafion SAC-13 or MMKT-K10 into High Energy Density Jet Fuel. Producer gas used in the process may come from sources that include gasification of waste feedstock and/or biomass residue feedstock, or waste gas from industrial processes, or methane containing gases including by not limited to natural gas, biogas, and/or landfill gas. In some embodiment, methane may be converted to liquid fuel, using engineered microorganisms and methods described herein.

In some embodiments, the inventive subject matter comprises an engineered microorganism with one or more exogenous genes including but not limited to limonene synthase. In some embodiments, the microorganism of the inventive subject matter is selected from the *Ralstonia* microorganisms. In some embodiments, the microorganism is *Ralstonia eutropha*. In some embodiments, the microorganism is selected from *Cupriavidus* microorganisms. In some embodiments, the microorganism is *Cupriavidus necator*. In some embodiments, the microorganism is *Cupriavidus necator* DSM531. In some embodiments the microorganism is selected from the genus *Hydrogenobacter*. In some embodiments the microorganism is *Hydrogenobacter thermophilus*. In some embodiments the microorganism contains the reverse tricarboxylic acid cycle (rTCA), also known as the reverse citric acid cycle or the reverse Krebs cycle.

In some embodiments the microorganism is *Rhodococcus opacus* or *Rhodococcus jostii* or *Rhodococcus* sp. In some embodiments the microorganism is *Hydrogenovibrio marinus*. In some embodiments the microorganism is *Rhodopseudomonas capsulata, Rhodopseudomonas palustris*, or *Rhodobacter sphaeroides*. In some embodiments the microorganism is an oxyhydrogen or knallgas strain. In some embodiments the microorganisms comprise one or more of the following knallgas microorganisms: *Aquifex pyrophilus* and *Aquifex aeolicus* or other *Aquifex* sp.; *Cupriavidus necator* or *Cupriavidus metallidurans* or other *Cupriavidus* sp.; *Corynebacterium autotrophicum* or other *Corynebacterium* sp.; *Nocardia autotrophica* and *Nocardia opaca* and other *Nocardia* sp.; purple non-sulfur photosynthetic bacteria including but not limited to *Rhodopseudomonas palustris, Rhodopseudomonas capsulata, Rhodopseudomonas viridis, Rhodopseudomonas sulfoviridis, Rhodopseudomonas blastica, Rhodopseudomonas spheroides, Rhodopseudomonas acidophila* and other *Rhodopseudomonas* sp., *Rhodospirillum rubrum*, and other *Rhodospirillum* sp.; *Rhodococcus opacus* and other *Rhodococcus* sp.; *Rhizobium japonicum* and other *Rhizobium* sp.; *Thiocapsa roseopersicina* and other *Thiocapsa* sp.; *Pseudomonas facilis* and *Pseudomonas flava* and *Pseudomonas putida* and *Pseudomonas hydrogenovora, Pseudomonas hydrogenothermophila, Pseudomonas palleronii* and *Pseudomonas pseudoflava* and *Pseudomonas saccharophila* and *Pseudomonas thermophila* and other *Pseudomonas* sp.; *Hydrogenomonas pantotropha, Hydrogenomonas eutropha, Hydrogenomonas facilis*, and other *Hydrogenomonas* sp.; *Hydrogenobacter thermophilus* and *Hydrogenobacter halophilus* and *Hydrogenobacter hydrogenophilus* and other *Hydrogenobacter* sp.; *Hydrogenophilus islandicus* and other *Hydrogenophilus* sp.; *Hydrogenovibrio marinus* and other *Hydrogenovibrio* sp.; *Hydrogenothermus marinus* and other *Hydrogenothermus* sp.; *Helicobacter pylori* and other *Helicobacter* sp.; *Xanthobacter autotrophicus* and *Xanthobacter flavus* other *Xanthobacter* sp.; *Hydrogenophaga flava* and *Hydrogenophaga palleronii* and *Hydrogenophaga pseudoflava* and other *Hydrogenophaga* sp.; *Bradyrhizobium japonicum* and other *Bradyrhizobium* sp.; *Ralstonia eutropha* and other *Ralstonia* sp.; *Alcaligenes eutrophus* and *Alcaligenes facilis* and *Alcaligenes hydrogenophilus* and *Alcaligenes latus* and *Alcaligenes paradoxus* and *Alcaligenes ruhlandii* and other *Alcaligenes* sp.; *Amycolata* sp.; *Aquaspirillum autotrophicum* and other *Aquaspirillum* sp.; *Arthrobacter* strain 11/X and other *Arthrobacter* sp.; *Azospirillum lipoferum* and other *Azospirillum* sp.; *Variovorax paradoxus*, and other *Variovorax* sp.; *Acidovorax facilis*, and other *Acidovorax* sp.; *Bacillus schlegelii* and *Bacillus tusciae* and other *Bacillus* sp.; *Calderobacterium hydrogenophilum* and other *Calderobacterium* sp.; *Derxia gummosa* and other *Derxia* sp.; *Flavobacterium autothermophilum* and other *Flavobacterium* sp.; *Microcyclus aquaticus* and other *Microcyclus; Mycobacterium gordoniae* and other *Mycobacterium* sp.; *Paracoccus denitrificans* and other *Paracoccus* sp.; *Persephonella marina* and *Persephonella guaymasensis* and other *Persephonella* sp.; *Renobacter vacuolatum* and other *Renobacter* sp.; *Thermocrinis ruber* and other *Thermocrinis* sp.; *Wautersia* sp.; cyanobacteria including but not limited to *Anabaena oscillarioides, Anabaena spiroides, Anabaena cylindrica*, and other *Anabaena* sp.; green algae including but not limited to *Scenedesmus obliquus* and other *Scenedesmus* sp., *Chlamydomonas reinhardii* and other *Chlamydomonas* sp., *Ankistrodesmus* sp., *Raphidium polymorphium* and other

*Rhaphidium* sp; as well as a consortiums of microorganisms that include oxyhydrogen microorganisms.

A number of different microorganisms have been characterized that are capable of growing on carbon monoxide as an electron donor and/or carbon source (i.e. carboxydotrophic microorganisms). In some cases carboxydotrophic microorganisms can also use H2 as an electron donor and/or grow mixotrophically. In some cases the carboxydotrophic microorganisms are facultative chemolithoautotrophs [Biology of the Prokaryotes, edited by J Lengeler, G. Drews, H. Schlegel, John Wiley & Sons, Jul. 10, 2009]. In some embodiments the microorganisms comprise one or more of the following carboxydotrophic microorganisms: *Acinetobacter* sp.; *Alcaligenes carboxydus* and other *Alcaligenes* sp.; *Arthrobacter* sp.; *Azomonas* sp.; *Azotobacter* sp.; *Bacillus schlegelii* and other *Bacillus* sp.; *Hydrogenophaga pseudoflava* and other *Hydrogenophaga* sp.; *Pseudomonas carboxydohydrogena* and *Pseudomonas carboxydovorans* and *Pseudomonas compransoris* and *Pseudomonas gazotropha* and *Pseudomonas thermocarboxydovorans* and other *Pseudomonas* sp.; *Rhizobium japonicum* and other *Rhizobium* sp.; *Streptomyces* G26 and other *Steptomyces* sp. In certain embodiments of the present invention a carboxydotrophic microorganism is used. In certain embodiments a carboxydotrophic microorganism that is capable of chemolithoautotrophy is used. In certain embodiments a carboxydotrophic microorganism that is able to use H2 as an electron donor in respiration and/or biosynthesis is used.

In some embodiments the microorganisms comprise obligate and/or facultative chemoautotrophic microorganisms including one or more of the following: *Acetoanaerobium* sp.; *Acetobacterium* sp.; *Acetogenium* sp.; *Achromobacter* sp.; *Acidianus* sp.; *Acinetobacter* sp.; *Actinomadura* sp.; *Aeromonas* sp.; *Alcaligenes* sp.; *Alcaligenes* sp.; *Arcobacter* sp.; *Aureobacterium* sp.; *Bacillus* sp.; *Beggiatoa* sp.; *Butyribacterium* sp.; *Carboxydothermus* sp.; *Clostridium* sp.; *Comamonas* sp.; *Dehalobacter* sp.; *Dehalococcoide* sp.; *Dehalospirillum* sp.; *Desulfobacterium* sp.; *Desulfomonile* sp.; *Desulfotomaculum* sp.; *Desulfovibrio* sp.; *Desulfurosarcina* sp.; *Ectothiorhodospira* sp.; *Enterobacter* sp.; *Eubacterium* sp.; *Ferroplasma* sp.; *Halothibacillus* sp.; *Hydrogenobacter* sp.; *Hydrogenomonas* sp.; *Leptospirillum* sp.; *Metallosphaera* sp.; *Methanobacterium* sp.; *Methanobrevibacter* sp.; *Methanococcus* sp.; *Methanosarcina* sp.; *Micrococcus* sp.; *Nitrobacter* sp.; *Nitrosococcus* sp.; *Nitrosolobus* sp.; *Nitrosomonas* sp.; *Nitrosospira* sp.; *Nitrosovibrio* sp.; *Nitrospina* sp.; *Oleomonas* sp.; *Paracoccus* sp.; *Peptostreptococcus* sp.; *Planctomycetes* sp.; *Pseudomonas* sp.; *Ralstonia* sp.; *Rhodobacter* sp.; *Rhodococcus* sp.; *Rhodocyclus* sp.; *Rhodomicrobium* sp.; *Rhodopseudomonas* sp.; *Rhodospirillum* sp.; *Shewanella* sp.; *Streptomyces* sp.; *Sulfobacillus* sp.; *Sulfolobus* sp.; *Thiobacillus* sp.; *Thiomicrospira* sp.; *Thioploca* sp.; *Thiosphaera* sp.; *Thiothrix* sp.; sulfur-oxidizers; hydrogen-oxidizers; iron-oxidizers; acetogens; and methanogens; consortiums of microorganisms that include chemoautotrophs; chemoautotrophs native to at least one of hydrothermal vents, geothermal vents, hot springs, cold seeps, underground aquifers, salt lakes, saline formations, mines, acid mine drainage, mine tailings, oil wells, refinery wastewater, coal seams, deep sub-surface; waste water and sewage treatment plants; geothermal power plants, sulfatara fields, and soils; and extremophiles selected from one or more of thermophiles, hyperthermophiles, acidophiles, halophiles, and psychrophiles.

In some embodiments the microorganism is a methanotroph. In some embodiments the microorganism is in the genus *Methylococcus*. In some embodiments the microorganism is *Methylococcus capsulatus*. In some embodiments the microorganism is a methylotroph. In some embodiments the microorganism is in the genus *Methylobacterium*. In some embodiments the microorganism is drawn from one or more of the following species: *Methylobacterium zatmanii*; *Methylobacterium extorquens*; *Methylobacterium chloromethanicum*. In some embodiments the microorganism is a methylotroph that naturally produces one or more triterpenes. In some embodiments the microorganisms is a methylotroph that naturally produces one or more of lupenone, lupeol, or lupane-type triterpenoids.

In some embodiments, the inventive subject matter converts producer gas including but not limited to syngas, biogas, tailgas, fluegas, CO, $CO_2$, $H_2$, and mixtures thereof. In some embodiments the heat content of the producer gas is at least 100 BTU per standard cubic foot (scf). In some embodiments of the present invention, a bioreactor is used to contain and grow the microorganisms, which is equipped with fine-bubble diffusers and/or high-shear impellers for gas delivery.

In some embodiments oxygen is used as an electron acceptor in the respiration of the microorganism used in the embodiment for the biosynthesis of limonene and/or other monoterpenes. In some embodiments strong electron acceptors including but not limited to $O_2$ are used to maximize efficiency and yield of products along anabolic pathways such as the isoprenoid pathways used to produce high energy density molecules such as limonene and/or other monoterpenes. A key challenge with using $O_2$ as an electron acceptor is keeping $O_2$ levels sufficiently adequate to allow aerobic microbes to grow well and generate anabolic products while also maintaining appropriate and safe levels of inflammable $H_2$ and $O_2$ mixtures in the bioreactor to minimize the risk of explosion. In some embodiments custom or specialized reactor designs are used to control $O_2$ in the broth at a level that is optimal for the microbes while avoiding dangerous gas mixes. In some embodiments bioreactor designs are used that avoid dangerous mixtures of $H_2$ and $O_2$ by exploiting the low solubility of $H_2$ and $O_2$ in water, while providing the microorganisms with necessary levels of these gases for cellular energy, carbon fixation, and limonene and/or monoterpene product generation.

Oxyhydrogen microorganisms generally have an advantage over strict anaerobic acetogenic or methanogenic microorganisms for carbon capture applications due to the higher oxygen tolerance of oxyhydrogen microorganisms. Since industrial flue gas is one intended source of $CO_2$ for certain embodiments of the present invention, the relatively high oxygen tolerance of oxyhydrogen microorganisms, as compared with obligately anaerobic methanogens or acetogens, can allow the $O_2$ content of 2-6% found in typical fluegas to be tolerated.

In some embodiments the inventive subject matter includes a recombinant microorganism that converts methanol to limonene and/or another monoterpenes.

In some embodiments the limonene or other monoterpene is converted to a HED jet fuel that has 10% or higher volumetric energy density than JP-8 jet fuel. In some embodiments a HED jet fuel is produced from producer gas, or gas mixtures containing $H_2$ and $CO_2$ and/or CO and/or $CH_4$ at a lower cost than an equivalent volume of JP-10 on an energy basis.

In some embodiments a $CO_2$-to-monoterpene pathway is enabled in a microorganism of the *Ralstonia* or *Cupriavidus* genus. The non-mevalonate or methyl-erythritol-4-phosphate (MEP) pathway for isoprenoid biosynthesis exists in *Ralstonia* and many other knallgas microorganisms (FIG. 1).

Figure 9:
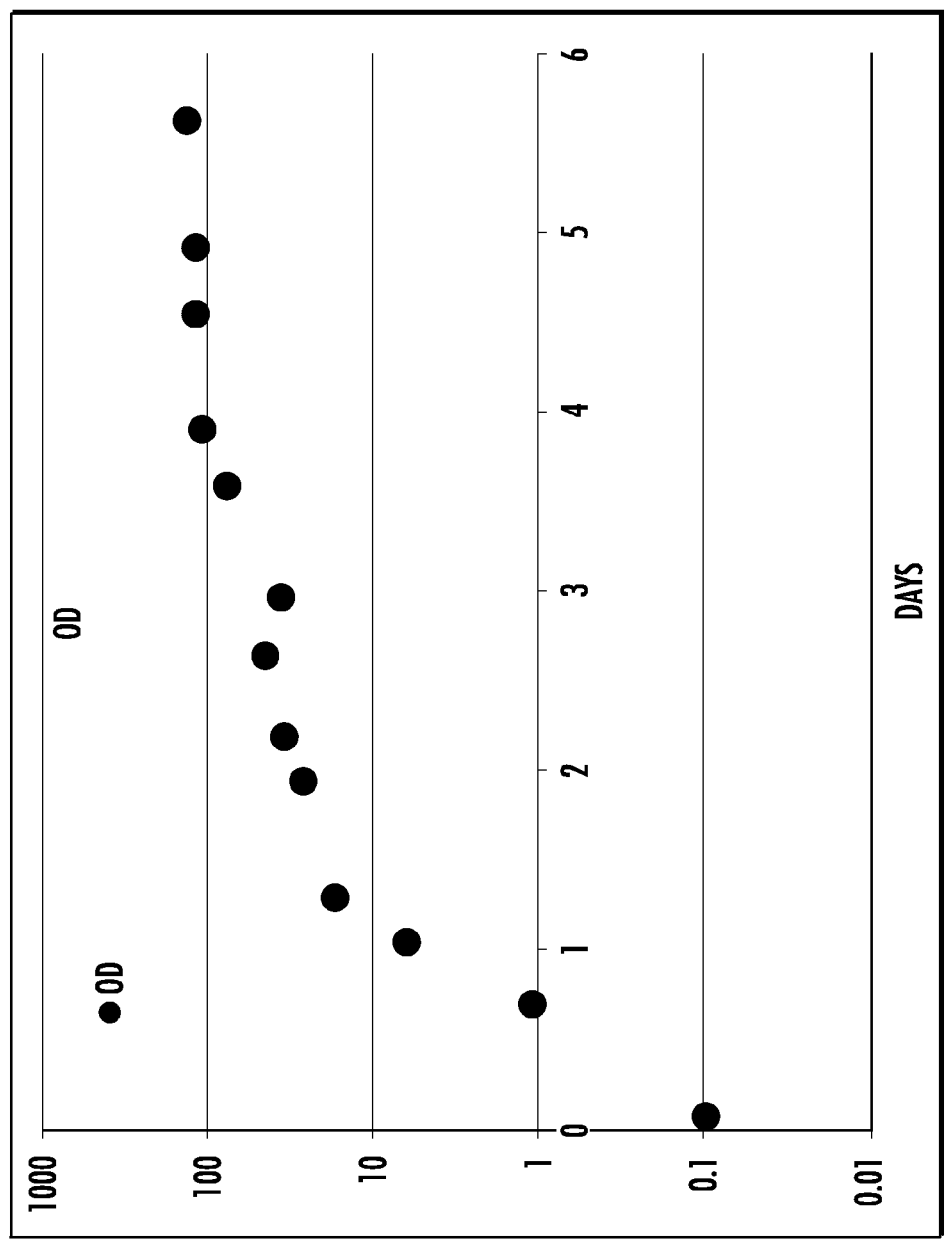
FIG. 9: Growth curve for Cupriavidus necator, as described in Example 2.

However, they lack enzymes for biosynthesis of high-energy monoterpenes such as pinene, limonene, which are all promising hydrocarbon fuel alternatives. In some embodiments Ralstonia or Cupriavidus are engineered for the production of limonene, and/or phellandrene. In some embodiments the carbon flux in the cell is redirected from naturally occurring cell products to limonene using methods known in the field of metabolic engineering. In some embodiments the cell is a Ralstonia or Cupriavidus microorganism. In some embodiments the production of limonene by a cell of the present invention is accomplished by the addition of a single-step reaction downstream of geranyl pyrophospate (GPP) in the MEP pathway catalyzed by (4S)-limonene synthase (LS; EC 4.2.3.16; FIG. 9). In some embodiments the production of limonene by a cell of the present invention is accomplished by the addition of a single-step reaction downstream of geranyl pyrophospate (GPP) in the MEP pathway catalyzed by (4R)-limonene synthase. In some embodiments the coding sequence (CDS) of the LS gene from Mentha spicata (Spearmint; GenBank: JX555975.1) is codon optimized for expression in a cell of the present invention. In some embodiments that cell is Ralstonia or Cupriavidus.

Efflux Pumps

In some embodiments the limonene yield is further enhanced by the engineering of efflux pumps. Efflux pumps are a common strategy used by bacteria to address small molecule toxicity. (Poole K (2005) J Antimicrob Chemoth 56: 20-51) Cupriavidus necator includes three such pumps with high homology to the E. coli and A. borkumensis (Ab) proteins identified in the patent number U.S. Ser. No. 13/115,925 Dunlop et al (FIG. 2). This includes high homology in the periplasmic loops that select molecules to be exported. (Eda S et al (2003) J Biol Chem 278: 2085-2088; Elkins C A, et al. (2002) J Bacteriol 195: 6490-6498)

As the general mechanism for microbicide tolerance is already present in Cupriavidus necator, AcrB and the Ab pump may be transferred to the microbe. In some embodiments AcrB and the Ab pumps are transferred into the microbe of the present invention. In some embodiments the microbe is Cupriavidus necator. In some embodiments overexpression of the native efflux pumps lead to increase of limonene tolerance in the microorganism of the present invention. In some embodiments the microorganism engineered for overexpression of native efflux pumps is Cupriavidus necator.

In some embodiments secretion of the monoterpene molecules will physically and kinetically sequester the monoterpene from cellular metabolism, continuously pushing the synthesis reaction forward and preventing monoterpene products from accumulating to toxic levels in the cell.

In some embodiments the inventive subject matter comprises a microbial organism having at least one exogenous nucleic acid encoding a (4S)-limonene synthase enzyme. In some embodiments the inventive subject matter comprises a microbial organism having at least one exogenous nucleic acid encoding a (4R)-limonene synthase enzyme. In some embodiments the microorganisms are selected from engineered Cupriavidus sp. (also known as Ralstonia sp.). In some embodiments the microbial organism is Cupriavidus necator (also known as Ralstonia eutropha). In some embodiments the microorganism is selected from the genus Hydrogenobacter. In some embodiments the microorganism is Hydrogenobacter thermophilus. In some embodiments the microorganism contains the reverse tricarboxylic acid cycle (rTCA), also known as the reverse citric acid cycle or the reverse Krebs cycle.

In some embodiments the microbial organism comprises an exogenous nucleic acid encoding an A. borkumensis YP_692684 protein. In some embodiments the microbial organism further comprises an E. coli AcrB protein.

In some embodiments the microbial organism comprises at least one exogenous nucleic acid encoding E. coli AcrB protein.

In some embodiments the microbial organism of the inventive subject matter comprises the ability to overexpress the native efflux pump YP_004685497. In some embodiments the microbial organism further comprises the ability to overexpress the native efflux pump YP_004687455 and YP_004685497. In some embodiments the microbial organism comprises the ability to overexpress the native efflux pump YP_004687080 and YP_004685497.

In some embodiments the microbial organism of the inventive subject matter comprises the ability to overexpress the native efflux pump YP_004687455. In some embodiments the microbial organism comprises the ability to overexpress the native efflux pump YP_004687455 and YP_004687080.

In some embodiments the microbial organism of the inventive subject matter comprises the ability to overexpress the native efflux pump YP_004687080.

Limonene and the similar cyclic C10 monoterpene phellandrene are both highly hydrophobic and in some embodiments, limonene and/or phellandrene that is secreted from the cells may accumulate as floater molecules on the surface layer of the medium (Metabolic engineering of Escherichia coli for limonene and perillyl alcohol production. Metabolic engineering, Vol. 19 (September 2013), pp. 33-41 by Jorge Alonso-Gutierrez, Rossana Chan, Tanveer S. Batth, et al.; Paradigm of Monoterpene (β-phellandrene) Hydrocarbons Production via Photosynthesis in Cyanobacteria In BioEnergy Research, Vol. 6, No. 3. (2013), pp. 917-929, doi: 10.1007/s12155-013-9325-4 by Fiona K Bentley, Jose Gines García-Cerdán, Hsu-Ching Chen, Anastasios Melis)

In some embodiments of this invention limonene is secreted from the cell of the present invention. In some embodiments this spontaneous separation of the limonene molecules from the cells alleviates the toxic effects of limonene by keeping intracellular levels low, preventing feedback inhibition of the biosynthetic pathway, thereby promoting the forward reaction. In some embodiments this reduces or eliminates the cost of cell harvesting and fracturing. In some embodiments partitioning of limonene to the medium is further facilitated by adding an organic phase such as dodecane to the culture to trap the molecule. Using this approach, and by continued metabolic engineering of the limonene biosynthetic pathway, Keasling and colleagues recently reported production of D-limonene in E. coli cultures at a titer of 435 mg L-1 without cell-adverse adverse effects (Metabolic engineering of Escherichia coli for limonene and perillyl alcohol production. Metabolic engineering, Vol. 19 (September 2013), pp. 33-41 by Jorge Alonso-Gutierrez, Rossana Chan, Tanveer S. Batth, et al.)

This is 100 times higher than previously reported and demonstrates the potential for high-yield limonene production in bacteria. In some embodiments the rapid and efficient separation of limonene from the culture medium is accomplished through two-phase systems known in the art. In some embodiments solvent-free non-lethal filtration and separation methods are used. In some embodiments a gravity separation unit is used to extract floatable product. In some embodiments the limonene containing broth flows from a bioreactor to a separation unit having a retention time that has been set to allow limonene to float to the top, and cell mass to settle out. In some embodiments the cell mass separated from the limonene is returned to the bioreactor for further production of limonene. In some embodiments the limonene emerges as discrete extracellular droplets, and gravity separation is used to promote sedimentation of the biomass and floatation of the limonene droplets. In some embodiments the separation vessel is sized on the basis of the terminal velocity of the limonene droplets and biomass. In some embodiments quiescent conditions are provided in the settling tank through the use of baffles and/or weirs. In some embodiments limonene and/or other monoterpenes does not separate from the biomass. In such embodiments the limonene and/or other monoterpenes are separated from the cell mass using methods known in the art including but not limited to solvent extraction.

In some embodiments of the present invention the biosynthesis of limonene and/or other monoterpenes that spontaneously partitios from aqueous medium combined with low cost gaseous feedstocks as input to the bioprocess such as producer gas, or $H_2$ and $CO_2$, and/or CO and/or $CH_4$ containing gas mixes improve the economic viability of monoterpene use as a biofuel. In some embodiments of the present invention the low cost of limonene product enabled by the invention totally disrupts the current limonene production from citrus peels, which is a very inefficient process. In some embodiments of the present invention the low cost of monoterpene (e.g, limonene production enables much wider use of monoterpenes (e.g., limonene), including as a fuel. In some embodiments of the present invention the production of limonene from a low cost, non-food based, highly scalable feedstock like natural gas enables larger scale production of limonene than from current sources. In some embodiments of the present invention, the invention is utilized for the production of limonene and/or other monoterpenes in regions where natural gas prices are lowest, and where remote, and particularly "stranded" and flared natural gas is known to occur such as in the U.S., Middle East, western Africa, and Russia. In some embodiments limonene and/or other monoterpenes are produced at a cost of less than $2 per gallon of gasoline energy equivalent (GGE). (the price of limonene in 2013 was $7/kg, which corresponds to over $20 per GGE). In some embodiments of the present invention the low cost of production of limonene enabled by the present invention would open whole new opportunities for the use of limonene that are at present completely proven to be technically feasible, but which are not economically viable due to the high cost of limonene using incumbent production methods.

Engineering Microorganisms with Limonene Synthesis Pathways

The inventive subject matter comprises, in one embodiment, an engineered knallgas microorganism capable of growing on syngas, or $H_2$ and $CO_2$, and/or CO, and/or $CO_4$, and/or other waste gases and capable of producing terpenes including but not limited to limonene.

Engineering of knallgas microorganisms is described in U.S. patent application Ser. No. 13/623,089, filed Sep. 19, 2012, and entitled "INDUSTRIAL FATTY ACID ENGINEERING GENERAL SYSTEM FOR MODIFYING FATTY ACIDS." This application is incorporated herein by reference in its entirety for all purposes.

Use of knallgas microorganisms for the conversion of syngas, producer gas, or other H2 and CO2 and/or CO containing gas mixes in high energy density molecules is described in a patent filed in the United States Patent and Trademark Office on Oct. 26, 2012 under Ser. No. 13/643,872, and entitled USE OF OXYHYDROGEN MICROORGANISMS FOR NON-PHOTOSYNTHETIC CARBON CAPTURE AND CONVERSION OF INORGANIC AND/OR C1 CARBON SOURCES INTO USEFUL ORGANIC COMPOUNDS. This application is incorporated herein by reference in its entirety for all purposes.

Use of chemotrophic microorganisms for the conversion of CO2 into useful organic chemicals is described in PCT international application number PCT/US2010/001402, filed May 12, 2010 and entitled BIOLOGICAL AND CHEMICAL PROCESS UTILIZING CHEMOAUTOTROPHIC MICROORGANISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS. This application is incorporated herein by reference in its entirety for all purposes.

Products from Limonene and Applications of Use Thereof

Limonene is a chemical with a pathway-to-commercialization that includes near-term small volume opportunities—because limonene is already used in products and commands a high per unit price—leading out to longer-term, high volume, low per unit prices applications, specifically fuel applications, made possible by the high energy density of limonene, as well as other beneficial characteristics it has for fuel applications.

Limonene that is produced biologically from gaseous substrates, using an engineered microorganism as described herein, may be converted to other products for numerous downstream uses.

Limonene to Jet Fuel

Limonene is readily dimerized with either Nafion SAC-13 or MMT-K10. (Meylemans et al. (2012), *Fuel* 97:60-568) Dimerization of limonene results in a HED Jet Fuel with similar properties to JP-10 as tested by the Naval Air Warfare Centre. The HED Jet Fuel has 10% higher volumetric energy density than JP-8 at a fraction of the cost of JP-10. In some embodiments limonene, produced in an engineered microorganism that is grown on a gaseous substrate, as described herein, is dimerized to produce HED jet fuel. In some embodiments, the limonene is dimerized using either Nafion SAC-13 or MMT-K10.

Solvent Replacement

In some embodiments the inventive subject matter further comprises using the limonene produced by the inventive process (e.g., production of limonene biologically in an engineered microorganism that is capable of converting a gaseous substrate to limonene, as described herein) as a solvent replacement. d-Limonene can directly replace components in existing solvent blends. (D-LIMONENE USES AND INDUSTRIES. The Nottingham Company, n.d. Web. http://www.ppiatlanta.com/pdfs/DataSheets/D-Limonene-%20uses.pdf) One example is the 1:1 substitution of d-Limonene in the place of xylene or 1,1,1 tri-chlor in blends with other inexpensive solvents to make up the balance (mineral spirits, isopropyl alcohol, butyl cello solve, etc.)

As a straight solvent, d-Limonene can replace a wide variety of products, including mineral spirits, methyl ethyl ketone, acetone, toluene, glycol ethers, and of course fluorinated and chlorinated organic solvents. ("What Is D-Limonene?" What Is D-Limonene? Florida Chemical Company, Inc., n.d. Web. 3 Oct. 2013. http://www.floridachemical.com/whatisd-limonene.htm) In some embodiments limonene is used to replace one or more of these organic solvents. As with most organic solvents, d-Limonene is not water soluble, so it can be used in the typical water separation units. In some embodiments limonene is used in a water separation unit. With a KB value of 67, d-Limonene has solubility properties dose to that of CFC's, indicating that it is a much better solvent than a typical mineral spirit. In some embodiments the superior characteristics of limonene to typical mineral spirits are exploited. Straight d-Limonene can be used as a wipe cleaner, in a dip bath, or in spray systems as a direct substitute for most other organic solvents. In some embodiments limonene produced through the present invention (e.g., via microbial production of limonene in an engineered microorganism that is grown on a gaseous substrate, as described herein) is used in one or more of these applications as a direct substitute for another organic solvent.

General Purpose Cleaners

In some embodiments the inventive subject matter further comprises using the limonene produced by the inventive process (e.g., production of limonene biologically in an engineered microorganism that is capable of converting a gaseous substrate to limonene, as described herein) in general purpose cleaners. Aqueous systems incorporating d-Limonene, surfactants, and water are especially popular for economic and environmental benefits. Levels of 3%-7% d-Limonene with surfactants (ethoxylated alcohols, glycol ethers, ethoxylated amines) are common for all-purpose cleaners. In some embodiments limonene produced through the present invention (e.g., via microbial production of limonene in an engineered microorganism that is grown on a gaseous substrate, as described herein) is mixed with surfactants (ethoxylated alcohols, glycol ethers, ethoxylated amines) for an all-purpose cleaner. Generally these formulas take a 2:1 ratio to emulsify d-Limonene at these levels (e.g. 10% d-Limonene, 5% surfactants, balance water). The addition of EDTA (chelates) to tie up metals, and phosphates (builders) such as STPP, TKPP, and metasilicates will contribute to the balance of the emulsion and probably significantly improve the overall effectiveness of the cleaner. These various ingredients can be adjusted to raise the pH to the desired level and improve chances of creating a stable "non-separating" formula. The 3%-7% d-Limonene level is effective on medium weight grease, oil, carbon and road film. It is an excellent whitewall tire cleaner in the concentrate form.

By combining d-Limonene with a surfactant package, a water diluting and rinsible solution can be made. In most cases these products are used in the institutional and household settings in place of caustic and other water based cleaners. A concentrated solution of a d-Limonene/surfactant solution can be made to be diluted before use, or pre-diluted solutions can be formed. The use concentrations of d-Limonene in these situations are usually 5-15%. In general these solutions are used as spray and wipe cleaners. The water dilutable solutions can also be used in industrial settings where a water rinse of the parts is desired to remove any residue which may remain.

In some embodiments limonene produced through the present invention (e.g., via microbial production of limonene in an engineered microorganism that is grown on a gaseous substrate, as described herein) will be used in one or more compositions and/or applications as described above in this section "General purpose cleaners".

Cleaner for Concrete

In some embodiments the inventive subject matter further comprises using the limonene produced by the inventive process (e.g., production of limonene biologically in an engineered microorganism that is capable of converting a gaseous substrate to limonene, as described herein) as a cleaner for concrete. d-Limonene has been used as a maintenance cleaner for concrete pads, parking complexes, and airport runways. The oils and greases that drip from cars can be lifted off the concrete either with a straight d-Limonene or a water diluted product. With straight d-Limonene, the product is put on the oil spots, which lifts the oil from the surface, and can be absorbed with a solid media such as kitty litter or oil absorptive pads. When using a water diluted product, the traditional mop-and-bucket method may be used. Some d-Limonene/water products have also been used in small floor scrubbers for removing oil and fork lift tire marks, and in larger units for taking up tire marks on runways. d-Limonene will usually clean graffiti (including effectively replacing xylene in graffiti removers) off concrete because of its ability to remove paint. The effectiveness of graffiti cleaning products can also be enhanced by combining n-methyl pyrollidone (NMP) with d-Limonene in a formulation. Strong enamels and epoxy paints will not usually be removed. State highway departments use d-Limonene to remove asphalt and tar from cement bridges.

In some embodiments limonene produced through the present invention (e.g., via microbial production of limonene in an engineered microorganism that is grown on a gaseous substrate, as described herein) will be used in one or more compositions and/or applications as described above in this section "Cleaner for concrete".

Release Agent for Asphalt

In some embodiments the inventive subject matter further comprises using the limonene produced by the inventive process (e.g., production of limonene biologically in an engineered microorganism that is capable of converting a gaseous substrate to limonene, as described herein) as a release agent. d-Limonene can be used at various levels for a release agent that is sprayed on the beds of asphalt trucks before picking up their loads to facilitate easy unloading. In the release agent application, d-Limonene may be a good replacement for diesel fuels commonly used in this application that are less suited to be dumped on the ground. Since d-Limonene will not readily freeze (−142° F. freezing point), the product lends itself to underground storage through cold winters.

In some embodiments limonene produced through the present invention (e.g., via microbial production of limonene in an engineered microorganism that is grown on a gaseous substrate, as described herein) will be used in one or more compositions and/or applications as described above in this section "Release agent for asphalt".

Circuit Board Cleaner

In some embodiments the inventive subject matter further comprises using the limonene produced by the inventive process (e.g., production of limonene biologically in an engineered microorganism that is capable of converting a gaseous substrate to limonene, as described herein) as a circuit board cleaner replacing chlorofluorocarbons (CFC's). Regular grades of d-Limonene can be used alone for flux removal on circuit boards, but the d-Limonene may leave a slight film and does not flash off quickly. It can be used in combination with the other solvents to reduce CFC's or used straight when followed by an acetone or isopropyl alcohol rinse. High purity/low residue grades of d-Limonene are being introduced for PCB applications with some success, though cost of this material may be twice that of regular d-Limonene.

In some embodiments limonene produced through the present invention (e.g., via microbial production of limonene in an engineered microorganism that is grown on a gaseous substrate, as described herein) will be used in one or more compositions and/or applications as described above in this section "Circuit board cleaner".

Grease Trap Maintainer

In some embodiments the inventive subject matter further comprises using the limonene produced by the inventive process (e.g., production of limonene biologically in an engineered microorganism that is capable of converting a gaseous substrate to limonene, as described herein) as a grease trap maintainer. d-Limonene helps dissolve grease (butter, cooking oils, meat fat, etc.) and keeps foul odors down in restaurant grease traps. Recommended formulations contain mostly d-Limonene with a small percent nonionic surfactant for partial emulsification (e.g. 90% d-Limonene and balance E-Z-Mulse™). Since d-Limonene is an oil, it will float on top of the water in the grease trap catch basin.

In some embodiments limonene produced through the present invention (e.g., via microbial production of limonene in an engineered microorganism that is grown on a gaseous substrate, as described herein) will be used in one or more compositions and/or applications as described above in this section "Grease trap maintainer".

Commercial Parts Washer

In some embodiments the inventive subject matter further comprises using the limonene produced by the inventive process (e.g., production of limonene biologically in an engineered microorganism that is capable of converting a gaseous substrate to limonene, as described herein) as a parts washer and in dip baths. In the typically parts washer founded in most truck and automobile maintenance and repair facilities, straight d-Limonene can be used as a replacement for petroleum derived products. Aside from the health benefits to the workers from working with a much less toxic solvent, d-Limonene has proven to be a more effective cleaner. As with any organic solvent in this type of application, gloves should be worn to protect against skin dryness and irritation. d-Limonene concentrates (e.g. 95% d-Limonene and 5% emulsifier) work well in closed automatic parts wash machines. The machines will dilute the concentrate automatically according to the quantity of water used in the wash cycle. Water-based concentrates do not work as well in this application because of a tendency to generate too much foam. Formulas should contain low foam or no foam surfactants (d-Limonene by itself depresses foam).

In some embodiments limonene produced through the present invention (e.g., via microbial production of limonene in an engineered microorganism that is grown on a gaseous substrate, as described herein) will be used in one or more compositions and/or applications as described above in this section "Commercial parts washer".

Spot and Stain Remover

In some embodiments the inventive subject matter further comprises using the limonene produced by the inventive process (e.g., production of limonene biologically in an engineered microorganism that is capable of converting a gaseous substrate to limonene, as described herein) as a spot and stain remover. The trick to successful spot and stain removal is to first evaluate the type of stain and then select the correct cleaning agent. d-Limonene concentrates (95% d-Limonene, 5% emulsifier) can effectively remove ink, oil, grease, paint, tar, bubble gum, and asphalt. After the spot has been wet with the cleaner, a water damp rag should be used to rinse the product from the area.

In some embodiments limonene produced through the present invention (e.g., via microbial production of limonene in an engineered microorganism that is grown on a gaseous substrate, as described herein) will be used in one or more compositions and/or applications as described above in this section "Spot and stain remover".

Hand Cleaners

In some embodiments the inventive subject matter further comprises using the limonene produced by the inventive process (e.g., production of limonene biologically in an engineered microorganism that is capable of converting a gaseous substrate to limonene, as described herein) as a hand cleaner. D-Limonene is very effective removing almost any soil including: ink, paint, grease, and tar. Solvent based hand cleaners usually contain approximately 30% solvent. At 10%, d-Limonene will out-perform most other solvent hand cleaners. Also the 10% level keeps cost competitive with traditional solvent-based systems at current limonene prices. In some embodiment of the present invention a lower cost limonene will be produced than current sources enabling higher levels of limonene in cost-competitive solvent hand cleaners. Generally, formulas require an equal percentage of surfactants to produce stable gel or lotion products. The addition of low levels of lanolin, jojoba oil, glycerin, or petrolatum reduces skin irritation associated with prolonged skin contact with d-Limonene. Many types of grit (gentle abrasives) besides pumice are sometimes added to heavy duty d-Limonene hand cleaners, including polyethylene beads and corn-cob grit.

In some embodiments limonene produced through the present invention (e.g., via microbial production of limonene in an engineered microorganism that is grown on a gaseous substrate, as described herein) will be used in one or more compositions and/or applications as described above in this section "Hand cleaners".

Cleaner for Printing Inks

In some embodiments the inventive subject matter further comprises using the limonene produced by the inventive process (e.g., production of limonene biologically in an engineered microorganism that is capable of converting a gaseous substrate to limonene, as described herein) as a cleaner for printing inks. This is an area where d-Limonene is currently having mixed success. Even though d-Limonene is excellent at cleaning and removing ink from rollers and presses, it sometimes may not be cost effective against straight cheap solvent systems, but if used properly and in the right formulation it can be more effective and approach economic equality with less expensive systems. In some embodiments of the present invention a lower cost limonene product will enable cost competitive cleaners with cheap solvent systems. For most oil and solvent based inks, it is recommended that you use straight d-Limonene. It will clean the ink from the rollers faster and with less solvent use than with a petroleum product. Drying time and the interval between cleaning and running are about the same. Some inks, especially the water and soy based, can easily be cleaned with a 20-25% solution of d-Limonene in water. Care must be taken when formulating these types of products to ensure the surfactants used for emulsification can be rinsed off the rollers. Generally, a mixture of 20-25% d-Limonene, 5-7% emulsifier (like an ethoxylated alcohol), and 4% of a rinsing agent such as Dowanol TPM works well. It should be noted that most rubber rollers can swell when in contact with d-Limonene for extended periods of time, so exposure of the rollers to the cleaner should be kept to a minimum.

In some embodiments limonene produced through the present invention (e.g., via microbial production of limonene in an engineered microorganism that is grown on a gaseous substrate, as described herein) will be used in one or more compositions and/or applications as described above in this section "Cleaner for printing inks".

Aerosol Ingredient

In some embodiments the inventive subject matter further comprises using the limonene produced by the inventive process (e.g., production of limonene biologically in an engineered microorganism that is capable of converting a gaseous substrate to limonene, as described herein) as an aerosol ingredient. d-Limonene can combine nicely with other aerosol dispenser propellants to impart a pleasant citrus odor. d-Limonene in aerosols can directly replace III tri-chlor, xylene, and other undesirable solvents included in sprays for cleaning and degreasing. d-Limonene may attack gaskets and valves of some conventional dispensers. Viton and neoprene may be some of the best choices for aerosol stem gaskets (better than butyl or buna). Valves and cans should have an epon (epoxy) coating. Aerosol packagers and gasket suppliers should be consulted on materials recommended for d-Limonene.

In some embodiments limonene produced through the present invention (e.g., via microbial production of limonene in an engineered microorganism that is grown on a gaseous substrate, as described herein) will be used in one or more compositions and/or applications as described above in this section "Aerosol ingredient".

Penetrating Oil

In some embodiments the inventive subject matter further comprises using the limonene produced by the inventive process (e.g., production of limonene biologically in an engineered microorganism that is capable of converting a gaseous substrate to limonene, as described herein) as a penetrating oil. d-Limonene can be used as a spray on product to loosen bolts and nuts, much like WD40™. d-Limonene has the ability to wick into tight joints and dissolve hardened greases and oils to assist in the removal of bound nuts and bolts.

In some embodiments limonene produced through the present invention (e.g., via microbial production of limonene in an engineered microorganism that is grown on a gaseous substrate, as described herein) will be used in one or more compositions and/or applications as described above in this section "Penetrating oil".

Adhesive Removal

In some embodiments the inventive subject matter further comprises using the limonene produced by the inventive process (e.g., production of limonene biologically in an engineered microorganism that is capable of converting a gaseous substrate to limonene, as described herein) as an adhesive removal. d-Limonene is a very good solvent for removal of adhesives from various substrates. Most contact adhesives will dissolve very quickly; however, d-Limonene has almost no effect on epoxies which have already cured.

In some embodiments limonene produced through the present invention (e.g., via microbial production of limonene in an engineered microorganism that is grown on a gaseous substrate, as described herein) will be used in one or more compositions and/or applications as described above in this section "Adhesive removal".

Marine Vessel Cleaning

In some embodiments the inventive subject matter further comprises using the limonene produced by the inventive process (e.g., production of limonene biologically in an engineered microorganism that is capable of converting a gaseous substrate to limonene, as described herein) as a marine vessel cleaning product. d-Limonene applications include degreasing diesel engines and bearings, removal of heavy carbon deposits, cleaning of slop hoses, cleaning and recycling of oil filters for extended life, and general-duty ship maintenance. d-Limonene should not interfere with oil and water separator sensor systems and is effective in oil water separators on large shipping vessels since d-Limonene and water separate so quickly. Additionally, d-Limonene has environmental advantages compared to other solvent-based systems. A concentration of 20 to 25% d-Limonene, 15% miscellaneous surfactants and other desired actives, and balance water. The full strength concentrate can be employed in 24 hour dips to remove heavy carbon deposits on engine parts and valves. The cleaner can be reused for a number of applications. Various dilutions of the concentrate can perform various other useful jobs: 1:10 dilution to clean oily water separator filters 1:20 dilution for slop hoses (to adequately clean slop hose so it can be reused) 1:50 dilution for general purpose cleaning around the ship.

In some embodiments limonene produced through the present invention (e.g., via microbial production of limonene in an engineered microorganism that is grown on a gaseous substrate, as described herein) will be used in one or more compositions and/or applications as described above in this section "Marine vessel cleaning".

Solvent Carriers

In some embodiments the inventive subject matter further comprises using the limonene produced by the inventive process (e.g., production of limonene biologically in an engineered microorganism that is capable of converting a gaseous substrate to limonene, as described herein) as a solvent carrier. Most paint and adhesive formulations use some sort of carrier solvent to disperse the product over the intended area. In many cases d-Limonene can be used as the carrier instead of mineral spirits or other petroleum based compounds, often with a resulting reduction in the volume of solvent used use. The drying times are generally not affected.

In some embodiments limonene produced through the present invention (e.g., via microbial production of limonene in an engineered microorganism that is grown on a gaseous substrate, as described herein) will be used in one or more compositions and/or applications as described above in this section "Solvent carriers".

Asphalt Grading

In some embodiments the inventive subject matter further comprises using the limonene produced by the inventive process (e.g., production of limonene biologically in an engineered microorganism that is capable of converting a gaseous substrate to limonene, as described herein) in asphalt grading. d-Limonene has been approved as a solvent for use in asphalt grading. When asphalt is being laid, every so many pounds must tested to insure that the proper mix of aggregate sizes and oils are being used. d-Limonene is very effective in the asphalt extraction methodology and has been approved by most highway departments.

In some embodiments limonene produced through the present invention (e.g., via microbial production of limonene in an engineered microorganism that is grown on a gaseous substrate, as described herein) will be used in one or more compositions and/or applications as described above in this section "Asphalt grading".

Chemical Synthesis

In some embodiments the inventive subject matter further comprises using the limonene produced by the inventive process (e.g., production of limonene biologically in an engineered microorganism that is capable of converting a gaseous substrate to limonene, as described herein) for the synthesis of other chemicals. d-Limonene is an interesting organic molecule to synthesize other compounds. Current commercial applications include production of tackifying terpene resins used in such diverse applications as adhesives for disposable baby diapers and floor coverings, and production of L-carvone, the imitation spearmint flavor used in many brands of toothpaste.

In some embodiments limonene produced through the present invention (e.g., via microbial production of limonene in an engineered microorganism that is grown on a gaseous substrate, as described herein) will be used in one or more compositions and/or applications as described above in this section "Chemical synthesis".

Pesticide

In some embodiments the inventive subject matter further comprises using the limonene produced by the inventive process (e.g., production of limonene biologically in an engineered microorganism that is capable of converting a gaseous substrate to limonene, as described herein) as a pesticide. d-Limonene can effectively kill ants, termites, and other insects on contact. Several popular flea dips for dogs and cats incorporate d-Limonene. d-Limonene can be an inert wetting agent in oil-based pesticides.

In some embodiments limonene produced through the present invention (e.g., via microbial production of limonene in an engineered microorganism that is grown on a gaseous substrate, as described herein) will be used in one or more compositions and/or applications as described above in this section "Pesticide".

Anti-Cancer Applications

In some embodiments the inventive subject matter further comprises using the limonene produced by the inventive process (e.g., production of limonene biologically in an engineered microorganism that is capable of converting a gaseous substrate to limonene, as described herein) in anti-cancer applications. Researchers at the University of Wisconsin and other institutions are studying the anti-cancer properties of d-Limonene, targeting potential applications to fight breast cancer in humans.

Early research suggests that limonene may be a potential anti-cancer ingredient and immune stimulant when consumed orally.

In some embodiments limonene produced through the present invention (e.g., via microbial production of limonene in an engineered microorganism that is grown on a gaseous substrate, as described herein) will be used in one or more compositions and/or applications as described above in this section "anti-cancer applications".

Odorant

In some embodiments the inventive subject matter further comprises using the limonene produced by the inventive process (e.g., production of limonene biologically in an engineered microorganism that is capable of converting a gaseous substrate to limonene, as described herein) as an odorant. d-Limonene has been used by the petroleum industry for years to make mercaptans for natural gas markers. The pleasant citrus aroma of d-Limonene can be incorporated into room air-fresheners, automobile air-fresheners, etc.

In some embodiments limonene produced through the present invention (e.g., via microbial production of limonene in an engineered microorganism that is grown on a gaseous substrate, as described herein) will be used in one or more compositions and/or applications as described above in this section "Odorant".

Extender

In some embodiments the inventive subject matter further comprises using the limonene produced by the inventive process (e.g., production of limonene biologically in an engineered microorganism that is capable of converting a gaseous substrate to limonene, as described herein) as an extender. Flavor and fragrance industry uses fairly large quantities of d-Limonene to extend other more valuable natural oils.

In some embodiments limonene produced through the present invention (e.g., via microbial production of limonene in an engineered microorganism that is grown on a gaseous substrate, as described herein) will be used in one or more compositions and/or applications as described above in this section "Extender".

Flavoring Food

In some embodiments the inventive subject matter further comprises using the limonene produced by the inventive process (e.g., production of limonene biologically in an engineered microorganism that is capable of converting a gaseous substrate to limonene, as described herein) to flavor food. D-Limonene is used in food manufacturing for flavoring purposes to add a delicate citrus taste. ("Limonene." *Squidoo*. N.p., n.d. Web. 3 Oct. 2013. http://www.squidoo.com/limonene)

In some embodiments limonene produced through the present invention (e.g., via microbial production of limonene in an engineered microorganism that is grown on a gaseous substrate, as described herein) will be used in one or more compositions and/or applications as described above in this section "Flavoring food".

Beauty Products

In some embodiments the inventive subject matter further comprises using the limonene produced by the inventive process (e.g., production of limonene biologically in an engineered microorganism that is capable of converting a gaseous substrate to limonene, as described herein) in beauty products as a scent in perfume and lotions, to clean skin, and to balance pH-levels of the skin.

In some embodiments limonene produced through the present invention (e.g., via microbial production of limonene in an engineered microorganism that is grown on a gaseous substrate, as described herein) will be used in one or more compositions and/or applications as described above in this section "Beauty products".

Antioxidant

In some embodiments the inventive subject matter further comprises using the limonene produced by the inventive process (e.g., production of limonene biologically in an engineered microorganism that is capable of converting a gaseous substrate to limonene, as described herein) as an antioxidant. d-limonene is known to boost immune function and protect cells, and has traditionally been used for weight loss and to treat bronchitis.

In some embodiments limonene produced through the present invention (e.g., via microbial production of limonene in an engineered microorganism that is grown on a gaseous substrate, as described herein) will be used in one or more compositions and/or applications as described above in this section "Anti-oxidant".

Miscellaneous

In some embodiments the inventive subject matter further comprises utilizing the limonene produced by the inventive process in the following applications and/or in compositions for the following applications in the appropriate proportions (Jones, Clarence L., 1984, Process for producing blended d-Limonene and uses of the blended product, U.S. patent Ser. No. 06/654,902):

Tar Remover—full strength;
Chewing Gum Remover—full strength;
Degreaser—full strength;

Cosmoline Remover—full strength;
Wax Remover—full strength;
Rust Remover—full strength;
Artist Oil Remover—full strength;
Typewriter Key Cleaner—full strength;
PVC Cleaner—full strength;
Decarbonizer—full strength;
Filter Cleaner—full strength;
Dead Paint Remover—full strength;
Carburetor Cleaner—full strength;
White Sidewall Cleaner—full strength;
Paint Brush Cleaner—full strength;
Disinfector—full strength;
Deodorizer—full strength or dilute with baby oil;
Tennis Shoe Cleaner—full strength or dilute with liquid soap;
Laundry additive—¼ to ½ cup per washer load;
Panel Cleaner—fill strength or dilute with liquid soap;
Black iron Pots and Pans—fill strength or dilute with liquid soap;
Mildew Remover—fill strength or dilute with liquid soap;
Oven, Stove, Pot Cleaner—full strength or dilute with liquid soap;
Tile Cleaner—full strength or dilute with liquid soap;
Crayon Remover—full strength;
Carpet spotter—full strength or dilute with shampoo;
Porcelain Cleaner—full strength or dilute with liquid soap;
Stainless Steel Cleaner—full strength or dilute with liquid soap;
Silver and Chrome Cleaner—full strength;
Jewelry Cleaner—full strength or add 25% ammonia;
Animal Stain Remover—full strength or dilute with liquid soap.

Petroleum Related Products

In some embodiments the inventive subject matter further comprises utilizing the limonene produced by the inventive process (e.g., production of limonene biologically in an engineered microorganism that is capable of converting a gaseous substrate to limonene, as described herein) in petroleum related applications. Because of is volatility and nature of composition, being basically a turpentine, dipentine, isopropyl compound of high hydrogen and carbon content, d-Limonene has a variety of petroleum related uses. These petroleum related uses would be areas wherein the addition of ammonia as a drying agent would be deleted from the process in producing the final product. d-Limonene is useful as a reclamation agent wherein it exhibits a remarkable ability to cleanse used crankcase oil by a process of percolation wherein the oil is weeped and percolated slowly through the d-Limonene liquid. In this process, the used crankcase oil is slowly introduced into a container containing the d-Limonene product and the oil is slowly weeped through the d-Limonene liquid in a constant flow. As the oil passes through the d-Limonene, it is preferably percolated to remain in contact with the d-Limonene product. This results in a process wherein the d-Limonene leaches out the high grade unbroken oil by a molecular adhesion of the high grade oil with the d-Limonene. This is a commingling action and allows the impurities in the crankcase oil to drain to the bottom of the container where they may be drained off. This mixture of high grade oil and d-Limonene need not be separated due to the high hydrogen and carbon content of the d-Limonene. This mixture is then a serviceable oil. The preferred range of d-Limonene to oil is large and is between 0.1% to 50%.

In some embodiments limonene produced through the present invention (e.g., via microbial production of limonene in an engineered microorganism that is grown on a gaseous substrate, as described herein) will be used in one or more compositions and/or applications as described above in this section "Petroleum related products".

Gasoline

In some embodiments the inventive subject matter further comprises utilizing the limonene produced by the inventive process (e.g., production of limonene biologically in an engineered microorganism that is capable of converting a gaseous substrate to limonene, as described herein) as a fuel additive. d-Limonene may be used as a fuel additive for diesel or gasoline where it is mixed and coalesces with gasoline and diesel of all grade levels. In spite of the carbon content in d-Limonene being dissimilar to petroleum carbons, the mixture exhibits an upgraded flammability due to the compatibility of d-Limonene with petroleum fuels. The mixture thus burns clean and without visual emissions. It also provides an excellent engine decarbonizer in that it has a tendency to dissolve petroleum carbons deposited on the engine surfaces and will not deposit its own carbons on engine surfaces under compression combustion. The use as an additive also prevents resin build-up in carburetors or injectors and is an aid in freeing stuck or restricted valves. The removal of carbon and prevention of resin build-up and freeing of stuck or restricted valves results in an increase in mileage. The preferred ratio is that of approximately one part d-Limonene to twenty parts diesel or gasoline.

In some embodiments limonene produced through the present invention (e.g., via microbial production of limonene in an engineered microorganism that is grown on a gaseous substrate, as described herein) will be used in one or more compositions and/or applications as described above in this section "Gasoline".

Uses in the Drilling and Refining Segments of the Petroleum Industry

In some embodiments the inventive subject matter further comprises utilizing the limonene produced by the inventive process (e.g., production of limonene biologically in an engineered microorganism that is capable of converting a gaseous substrate to limonene, as described herein) in both the drilling and refining segments of the petroleum industry. d-Limonene may be used to dissolve and suspend all forms of paraffin in solution in a variety of applications in the petroleum industry as indicated. The preferred concentration of the d-Limonene in this application is between sixty (60%) percent to one-hundred (100%) percent d-Limonene.

In some embodiments limonene produced through the present invention (e.g., via microbial production of limonene in an engineered microorganism that is grown on a gaseous substrate, as described herein) will be used in one or more compositions and/or applications as described above in this section "Uses in the drilling and refining segments of the petroleum industry".

Crankcase Additive

In some embodiments the inventive subject matter further comprises utilizing the limonene produced by the inventive process (e.g., production of limonene biologically in an engineered microorganism that is capable of converting a gaseous substrate to limonene, as described herein) as a crankcase additive. d-Limonene is useful as a crankcase additive to prevent sludge and resin formation in the lubricant supply section of an internal combustion engine. The preferred range is one part of d-Limonene to every thirty-two parts of lubricant.

In some embodiments limonene produced through the present invention (e.g., via microbial production of limonene in an engineered microorganism that is grown on a gaseous substrate, as described herein) will be used in one or more compositions and/or applications as described above in this section "Crankcase additive".

Additive in Petroleum Solvents

In some embodiments the inventive subject matter further comprises utilizing the limonene produced by the inventive process (e.g., production of limonene biologically in an engineered microorganism that is capable of converting a gaseous substrate to limonene, as described herein) as an additive in petroleum solvents. d-Limonene is useful as an additive in petroleum solvents since it exhibits amazing performance in releasing rusted threads, pistons and valves in frozen engines, pumps, compressors, etc. In this use, the d-Limonene may be used at full strength or at a ratio of a ninety (90%) percent d-Limonene to ten (10%) percent oil.

In some embodiments limonene produced through the present invention (e.g., via microbial production of limonene in an engineered microorganism that is grown on a gaseous substrate, as described herein) will be used in one or more compositions and/or applications as described above in this section "Additive in petroleum solvents".

Refining Agent for Crude or Partially Refined Petroleums

In some embodiments the inventive subject matter further comprises utilizing the limonene produced by the inventive process (e.g., production of limonene biologically in an engineered microorganism that is capable of converting a gaseous substrate to limonene, as described herein) as a refining agent for crude or partially refined petroleums. d-Limonene may be used as a refining agent for all forms of crude or partially refined petroleums whereby it separates the petroleum products from water and separates the oil from undesirable particulates present. These undesirable particulates are normally comprised of solidified carbons, sulfur, etc. By the nature of the composition of d-Limonene, the oil or petroleum product is upgraded by the addition thereof due to its high compatibility with petroleum. This results from the fine grade citrus oil in the d-Limonene product.

In some embodiments limonene produced through the present invention (e.g., via microbial production of limonene in an engineered microorganism that is grown on a gaseous substrate, as described herein) will be used in one or more compositions and/or applications as described above in this section "Refining agent for crude or partially refined petroleums".

Chemical Conversions

Production of Alkanes Through Hydrogenation

In some embodiments the inventive subject matter further comprises hydrogenating the limonene produced by the inventive process (e.g., production of limonene biologically in an engineered microorganism that is capable of converting a gaseous substrate to limonene, as described herein). During hydrogenation, hydrogen plus a platinum catalyst is added to Limonene and breaks the double bond in limonene, producing an alkane. (Burdett, Edith. "Limonene." N.p., n.d. Web. http://www.docstoc.com/docs/23885504/Limonene---PowerPoint)

In some embodiments limonene produced through the present invention will be used in one or more applications as described above in this section "Production of alkanes through hydrogenation".

Production of Dihaloalkane by Halogenation

In some embodiments the inventive subject matter further comprises halogenation of the limonene produced by the inventive process (e.g., production of limonene biologically in an engineered microorganism that is capable of converting a gaseous substrate to limonene, as described herein). During halogenation a halogen such as bromine, chlorine, or iodine breaks the double bond of limonene and a dihaloalkane is produced.

In some embodiments limonene produced through the present invention (e.g., via microbial production of limonene in an engineered microorganism that is grown on a gaseous substrate, as described herein) will be used in one or more applications as described above in this section "Production of dihaloalkane by halogenation".

Production of Haloalkane by Hydrohalogenation

In some embodiments the inventive subject matter further comprises hydrohalogenation of the limonene produced by the inventive process (e.g., production of limonene biologically in an engineered microorganism that is capable of converting a gaseous substrate to limonene, as described herein). During hydrohalogenation hydrogen and a halogen break the double bond of limonene forming a haloalkane.

In some embodiments limonene produced through the present invention (e.g., via microbial production of limonene in an engineered microorganism that is grown on a gaseous substrate, as described herein) will be used in one or more applications as described above in this section "Production of haloalkane by hydrohalogenation".

Production of Alcohol by Hydration

In some embodiments the inventive subject matter further comprises hydrating the limonene produced by the inventive process (e.g., production of limonene biologically in an engineered microorganism that is capable of converting a gaseous substrate to limonene, as described herein). During the hydration reaction $H_2O$ breaks the double bond of limonene producing an alcohol.

In some embodiments limonene produced through the present invention (e.g., via microbial production of limonene in an engineered microorganism that is grown on a gaseous substrate, as described herein) will be used in one or more applications as described above in this section "Production of alcohol by hydration".

Enzymatic Conversion

Production of Trans-Isopiperitenol and Menthol

In some embodiments the inventive subject matter further comprises utilizing the limonene produced by the inventive process (e.g., production of limonene biologically in an engineered microorganism that is capable of converting a gaseous substrate to limonene, as described herein) to produce trans-Isopiperitenol which is then converted into menthol. Limonene is converted into trans-isopiperitenol and menthol either in a naturally occurring organism or an organism that produces limonene and is capable of being genetically engineered with the enzymes necessary to produce menthol. ("Menthol." Wikipedia, 10 Feb. 2013. Web. 4 Oct. 2013. https://en.wikipedia.org/wiki/Menthol) Limonene produced by the inventive process would then be converted by the natural organism or the genetically modified organism by the following pathway: limonene would be converted by 4S-limonene-3-hydroxylase to produce trans-Isopiperitenol. The enzyme trans-isopiperitenol dehydrogenase would then convert trans-Isopiperitenol into Isopiperitenone. The enzyme isopiperitenone reductase would then convert isopiperitenone into cis-isopulegone. The enzyme cis-isopulegone isomerase would then convert cis-isopulegone into Pulegone. The enzyme pulegone reductase would then convert Pulegone into menthone. The enzyme menthone reductase would then convert menthone into menthol.

Production of Trans-Carveol and Carvone

In some embodiments the inventive subject matter further comprises using the limonene produced by the inventive process (e.g., production of limonene biologically in an engineered microorganism that is capable of converting a gaseous substrate to limonene, as described herein) to produce trans-carveol which is then converted into carvone. Limonene is converted into trans-carveol and carvone either in a naturally occurring organism or an organism that produces limonene and is capable of being genetically engineered with the enzymes necessary to produce carveol or carvone. Limonene produced by the inventive process would then be converted by the natural organism or the genetically modified organism by the following pathway: limonene would be converted by 4S-limonene-6-hydroxylase to produce trans-carveol. Trans-carveol is then converted into carvone through a redox reaction. ("EC 1.1.1.243—Carveol Dehydrogenase." N.p., n.d. Web. 4 Oct. 2013. <http://www.brenda-enzymes.org/php/result_flat.php4?ecno=1.1.1.243>.)

Production of Para-Cymene, Terephthalic Acid, and Dimethyl Terephthalate

In some embodiments the inventive subject matter further comprises utilizing the limonene produced by the inventive process (e.g., production of limonene biologically in an engineered microorganism that is capable of converting a gaseous substrate to limonene, as described herein) to produce para-cymene which can then be converted into terephthalic acid which can then be converted into dimethyl terephthalate. Limonene, produced by the inventive process, is dehydrogenated with a catalyst, such as ethylenediamine and anhydrous $FeCl_3$ to produce para-cymene. (Berti C, Binassi E, Colonna M, Fiorini M, Kannan G, Karanam S, Mazzacurati M, Odeh I, Vannini M, Bio-based terephthalate polyesters. European Patent EP 2370491 A2)

Dehydrogenation can be caused by a catalyst selected from the group comprising of metal catalysts, amine catalysts, and combinations thereof. Para-cymene can be produced at a yield of 70% to 95% from limonene. Para-cymene can be further converted to terephthalic acid in the presence of an oxidation catalyst, such as potassium permanganate. Para-cymene can be converted to terephthalic acid substantially in the absence of chromium oxide, and substantially in the absence of chromium. Para-cymene can be converted to terephthalic acid in a two-step oxidation comprising a first step using a mineral acid, and a second step using a transition metal oxidant, which can produce a total yield of 85%.

Terephthalic acid can be further converted with methanol into dimethyl terephthalic acid.

Terephthalic acid can also be further converted through dehydrogenation to produce 1,4-cyclohexane dimenthol.

In some embodiments limonene produced through the present invention (e.g., via microbial production of limonene in an engineered microorganism that is grown on a gaseous substrate, as described herein) will be used in one or more applications as described above in this section "Production of para-cymene, terephthalic acid, and dimethyl terephthalate".

Production of Poly(Alkaline Terephthalate)s, Also Known as Polyesters

The terephthalic acid and dimethyl terephthalic acid derived from the limonene produced by the inventive process (e.g., production of limonene biologically in an engineered microorganism that is capable of converting a gaseous substrate to limonene, as described herein) may be converted by methods known to those of skilled in the art, such as a polycondensation reaction, or transesterification, or other methods known to those of skill in the art to produce a variety of poly(alkylene terephthalate)s, also known as polyesters. The terephthalic acid and dimethyl terephthalic acid derived from the limonene produced by the inventive process may also be further converted by a reaction with a diol (HO—R—OH) selected from the group consisting of alkyl, cycloalkyl, and cycloakylene diakyl groups having from two to ten carbons.

To produce poly(butylene terephthalate) (PBT) the terephthalic acid and dimethyl terephthalic acid, derived from the limonene produced by the inventive process, react with a diol having a four carbon chain.

To produce poly(trim ethylene terephthalate) (PTT) the terephthalic acid and dimethyl terephthalic acid, derived from the limonene produced by the inventive process, react with a diol having a three carbon chain.

To produce poly(ethylene terephthalate) (PET) the terephthalic acid and dimethyl terephthalic acid, derived from the limonene produced by the inventive process, react with a diol having a two carbon chain.

PET produced from derivatives of the inventive process can further be polymerized to produce longer molecular chains. ("Plastic Bottle Manufacturing." N.p., n.d. Web. 4 Oct. 2013. http://www.thomasnet.com/articles/materials-handling/plastic-bottle-manufacturing) This longer chain PET can then be heated and molded to produce bottles, carpet, film, or other plastic containers or consumer goods. One example of a process to produce plastic bottles is to heat the PET and place the PET in a mold assuming the shape of a long thin tube. The tube of PET, now called a parison, is then transferred into a second, bottle-shaped mold. A thin steel rod, called a mandrel is slid inside the parison where it fills the parison with highly pressurized air, and stretch blow molding begins: as a result of the pressurized air, heat and pressure, the parison is blown and stretched into the mold, assuming a bottle shape. To ensure the bottom of the bottle is consistently flat, a separate component of plastic is simultaneously joined to the bottle during blow molding. The mold must be cooled quickly for the bottle to set properly. The bottle can be cooled either directly or indirectly. Water can be coursed through pipes surrounding the mold, which indirectly cools the mold and plastic. Direct methods include using pressurized air or carbon dioxide directly on the mold and plastic. Once the bottle has been cooled and sets, it is removed from the mold. If a continuous molding process has been used, the plastic between the bottles will need to be trimmed to separate the bottles. Excess plastic in non-continuous processes may also need to be trimmed.

One example of a process to produce carpet from PET is through melt spinning. In melt spinning, the PET substance is melted for extrusion through a spinneret. ("Manufacturing: Fiber Formation Technology." N.p., n.d. Web. 8 Oct. 2013, http://www.fibersource.com/f-tutor/techpag.htm) A spinneret is a multi-pored device through which a plastic polymer melt is extruded to form fibers. (Spinneret (polymers). (2013, Aug. 23). In *Wikipedia, The Free Encyclopedia*. Retrieved 22:27, Oct. 8, 2013, from http://en.wikipedia.org/w/index.php?title=Spinneret_(polymers)&oldid=569917656) After going through the spinneret, the PET is directly solidified by cooling. The melt spun fibers can be extruded from the spinneret in different cross-sectional shapes including but not limited to round, trilobal, pentagonal, and octagonal. Pentagonal-shaped and hollow fibers, when used in carpet, show less soil and dirt. Octagonal-shaped fibers offer glitter-free effects. Hollow fibers trap air, creating insulation and provide loft characteristics equal to, or better than, down.

One example of a process to produce film from PET begins with a film of molten PET being extruded onto a chill roll, which quenches it into the amorphous state. (BoPET. (2013, Oct. 3). In *Wikipedia, The Free Encyclopedia*. Retrieved 23:12, Oct. 8, 2013, from http://en.wikipedia.org/w/index.php?title=BoPET&oldid=575532373) It is then biaxially oriented by drawing. The most common way of doing this is the sequential process, in which the film is first drawn in the machine direction using heated rollers and subsequently drawn in the transverse direction, i.e. orthogonally to the direction of travel, in a heated oven. It is also possible to draw the film in both directions simultaneously, although the equipment required for this is somewhat more elaborate. Draw ratios are typically around 3 to 4 in each direction. Once the drawing is completed, the film is "heat set" or crystallized under tension in the oven at temperatures typically above 200 degrees Celsius. The heat setting step prevents the film from shrinking back to its original unstretched shape and locks in the molecular orientation in the film plane. The orientation of the polymer chains is responsible for the high strength and stiffness of biaxially oriented PET film, which has a typical Young's modulus of about 4 GPa. Another important consequence of the molecular orientation is that it induces the formation of many crystal nuclei. The crystallites that grow rapidly reach the boundary of the neighboring crystallite and remains smaller than the wavelength of visible light. As a result, biaxially oriented PET film has excellent clarity, despite its semicrystalline structure. To make handling possible, microscopic inert inorganic particles are usually embedded in the PET to roughen the surface of the film. Biaxially oriented PET film can be metallized by vapor deposition of a thin film of evaporated aluminum, gold, or other metal onto it. The result is much less permeable to gasses (important in food packaging) and reflects up to 99% of light, including much of the infrared spectrum. For some applications like food packaging, the aluminized boPET film can be laminated with a layer of polyethylene, which provides sealability and improves puncture resistance. The polyethylene side of such a laminate appears dull and the PET side shiny. Other coatings, such as conductive indium tin oxide, can be applied to PET film by sputter deposition. Uses of PET films include but are not limited to: flexible packaging and food contact applications; covering over paper; insulating material; solar, marine, and aviation applications; electronic and acoustic applications; and graphic arts.

To produce poly(cyclohexylene dimethyl terephthalate) (PCT) the terephthalic acid and dimethyl terephthalic acid, derived from the limonene produced by the inventive process, react with 1,4-cyclohexanedimethanol.

In some embodiments limonene produced through the present invention (e.g., via microbial production of limonene in an engineered microorganism that is grown on a gaseous substrate, as described herein) will be used in one or more applications as described above in this section "Production of poly(alkaline terephthalate)s also known as polyesters".

The following examples are intended to illustrate, but not limit, the invention.

EXAMPLES

Example 1

*Cupriavidus necator* strain DSM 531 was grown on a mixture of $H_2$ and $CO_2$ and $O_2$ gases as the sole source of energy and carbon for growth.

The following protocol was followed for experiments performed using a mixture of gases in gas tight serum bottles.

Experimental inoculum: 5% by volume, taken from another $H_2$ grown serum bottle culture.

The initial $H_2$ grown serum bottle culture was given 5% inoculation from a Lysogeny broth (LB) grown *Cupriavidus necator* inoculum and grown ~72 hours on $H_2/CO_2/O_2$ gas mix following inoculation from original LB grown culture. Original LB grown inoculum was recovered from glycerol stock stored at −80° C.

Serum bottle growth on gas was performed in 160-ml stoppered and sealed Wheaton glass serum bottles (VWR product number 16171-385). Volume of liquid media was 20 ml. The bottles were plugged with a rubber stopper (VWR #100483-774) and aluminum seal (VWR #89047-008) using Wheaton Hand-Operated Crimper (VWR #80078-996). 20 ml working volume included 19 ml Minimal Salts Medium (MSM), as described in *Thermophilic Bacteria*, CRC Press, Boca Raton, Fla., Jacob K. Kristjansson, ed., 1992, p. 87, Table 4+1 ml inoculum (i.e., 5% inoculum).

The MSM was dispensed in the bottles and gaseous compounds were added as follows: Sterile MSM was transferred into bottles under sterile conditions. 5% gas cultured inoculum was inoculated into the bottles under sterile conditions, and the bottles were plugged with rubber stoppers and sealed. A gas mixture was added at 15 psig to the bottles through a manifold. After the gas mix was added, the seal was crimped with aluminum to seal the serum bottles. The bottles were then placed in a shake flask incubator.

The following experimental results were obtained from 16 serum bottles (14 experimental replicates, 2 controls) incubated at 30° C., 250 RPM. All 16 serum bottles were purged simultaneously with a 67% $H_2$, 24% air (4.8% $O_2$), 9% $CO_2$ gas mix using a manifold as described above. The gas composition run through the manifold was confirmed using gas chromatography (GC) before connecting the serum bottles. Bottles were sacrificed for analysis at 7 time points. The two negative controls were sacrificed at $T_0$ and the last time point respectively. Negative control bottles had identical preparation as experimental bottles minus the inoculum, and were used to detect any contamination and/or abiotic loss or leakage of gas from the bottle headspace. Gas headspace pressure readings samples were taken on negative controls to observe any abiotic $CO_2$ & $H_2$ sorption into the liquid medium and/or gas loss due to leakage.

Sampling and Analytical Procedures

All samples were taken under sterile conditions using syringes and needles for bottle experiments. The optical density (OD) was measured using a Beckman Coulter DU720 UV/Vis spectrophotometer at 650 nm using 100 ul samples.

At each time point one to three experimental replicate bottles were sacrificed for analysis. Gaseous consumption within the serum bottles was measured using a pressure gauge connected to a needle. The headspace gas pressure was measured for each sacrificed bottle, and a sample of headspace gas was taken by gas tight syringe for gas chromatography (GC) analysis. Analysis of gas headspace samples by GC used a 100-uL sample of headspace gas injected into the GC via gas tight syringe. Gas headspace content of $H_2$, $CO_2$, $O_2$, and $N_2$ in the serum bottles was quantified at each time point. For sampling the broth, the septum of serum bottle was wiped with EtOH and the entire liquid contents of bottle withdrawn into a 30 mL syringe, using bottle pressure. 100 uL of sample was pipetted out for OD measurement at 650 nm. Samples were centrifuged at 12000 G for 15 min at 4° C. Pellets were resuspended in 10 mL sterile PBS, vortexed, and vacuum filtered through pre-weighed 0.45 um filters. The filters were dried and filter+biomass retentate weighed to determine biomass dry weight. Dry weights were determined for cells collected on membrane filters (0.45 um) by drying at 60° C. for 24 hours and cooling to room temperature in a desiccator and weighing. This cycle of drying and re-weighing was continued until the weight remained constant. A correlation was developed between OD and biomass density (dry cell weight per volume).

Figure 5:
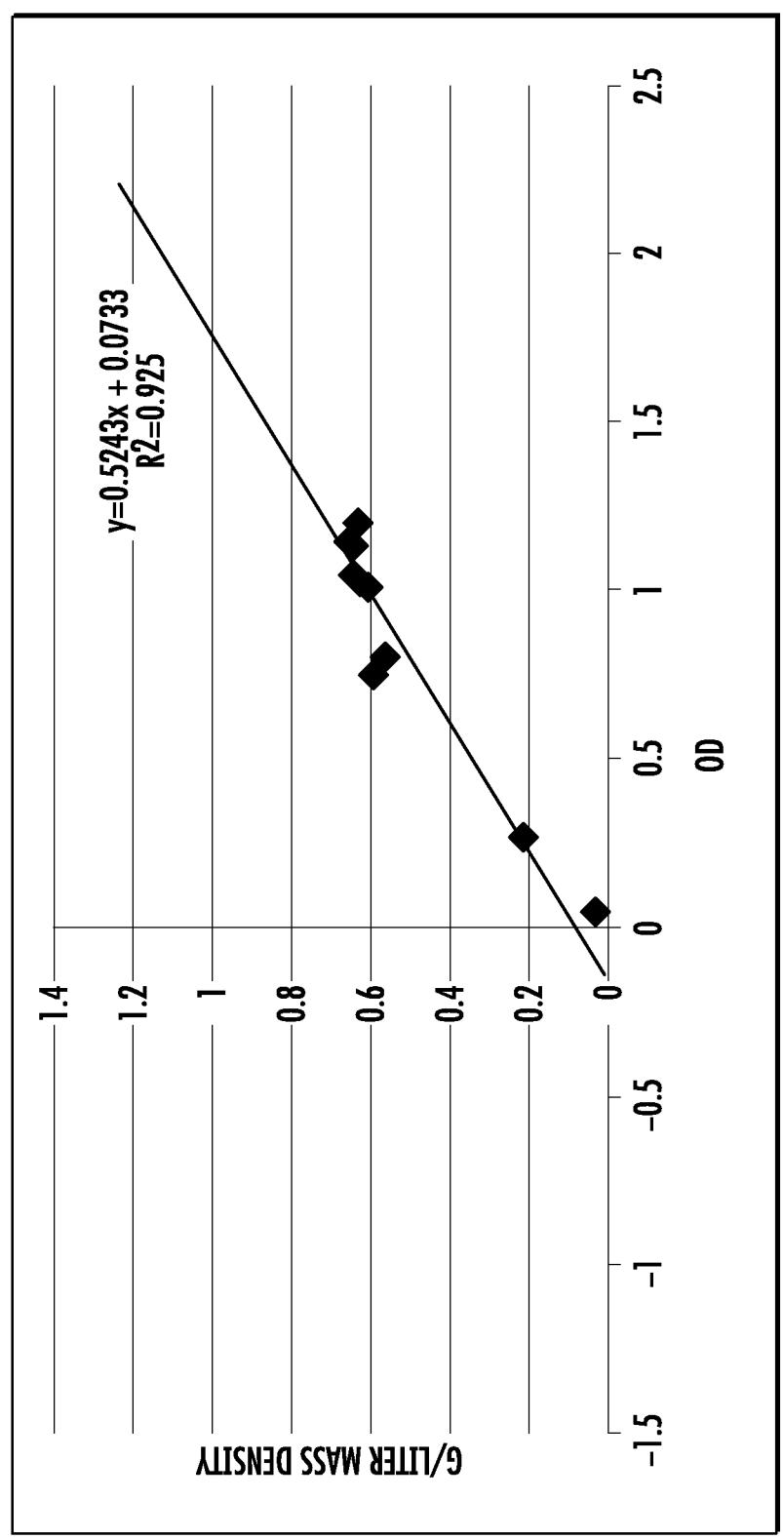
FIG. 5: Growth curve for Cupriavidus necator, as described in Example 1.
Figure 6:
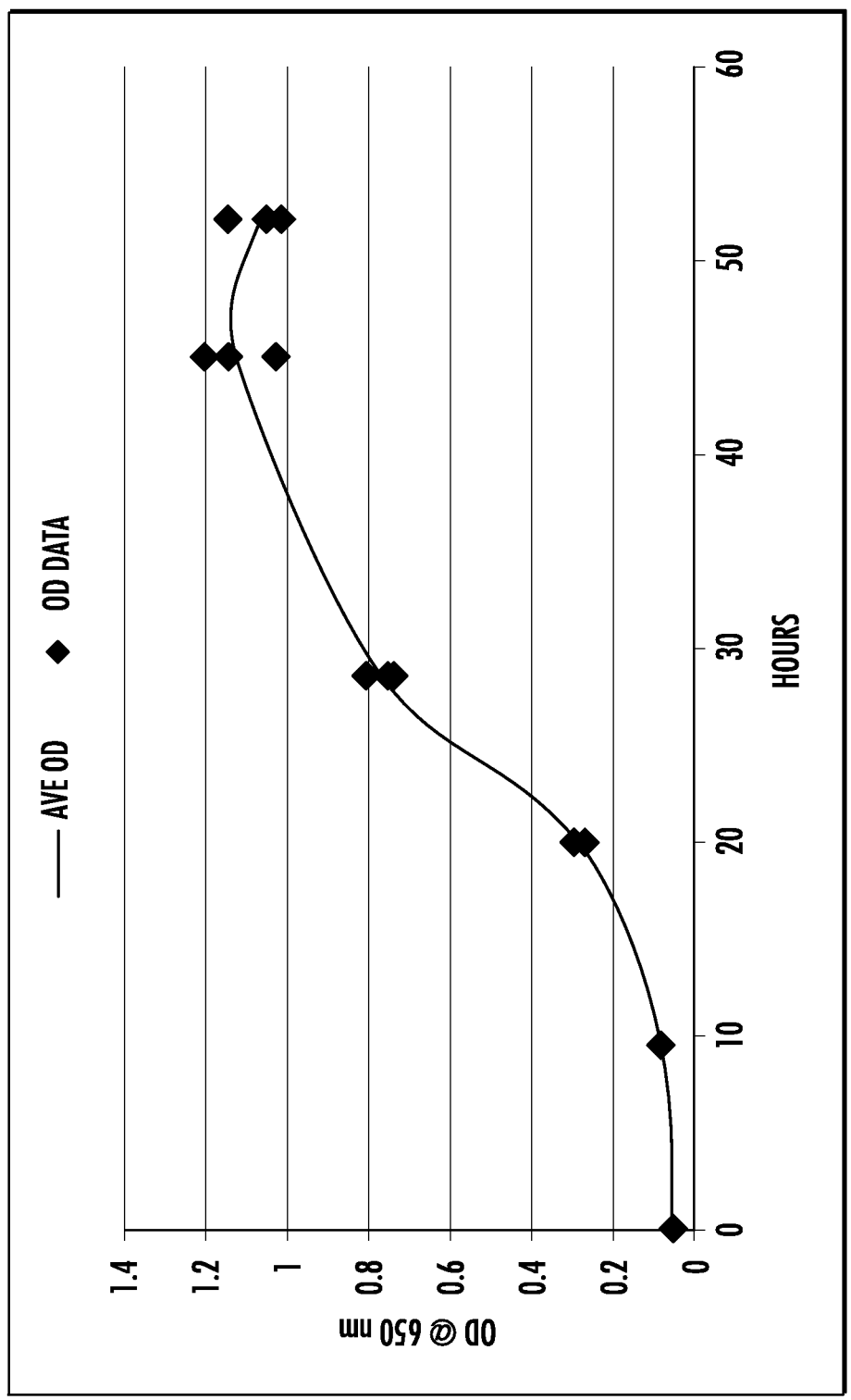
FIG. 6: Decrease in gas pressure over time, as described in Example 1.
Figure 7:
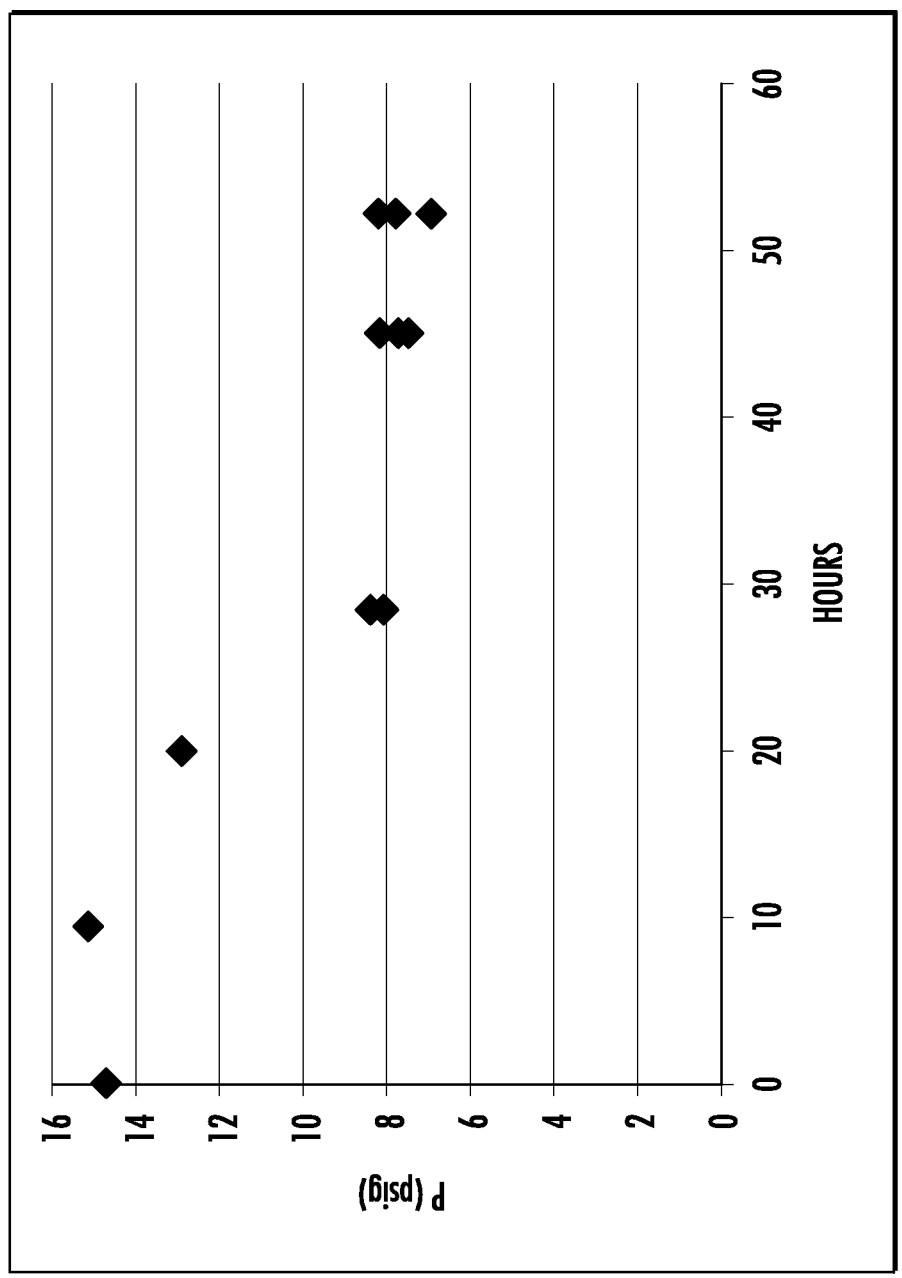
FIG. 7: Change in headspace gas pressure over time with growth, as described in Example 1.

The correlation between OD and biomass density is shown in FIG. 5. The growth curve for this experiment is shown in FIG. 6. The OD measured for individual experimental replicates is represented by the diamond symbols, and the average OD is represented by the solid line. Logarithmic growth occurred between 9 and 30 hours (FIG. 6). Change in headspace gas pressure over time is shown in FIG. 7.

Figure 8:
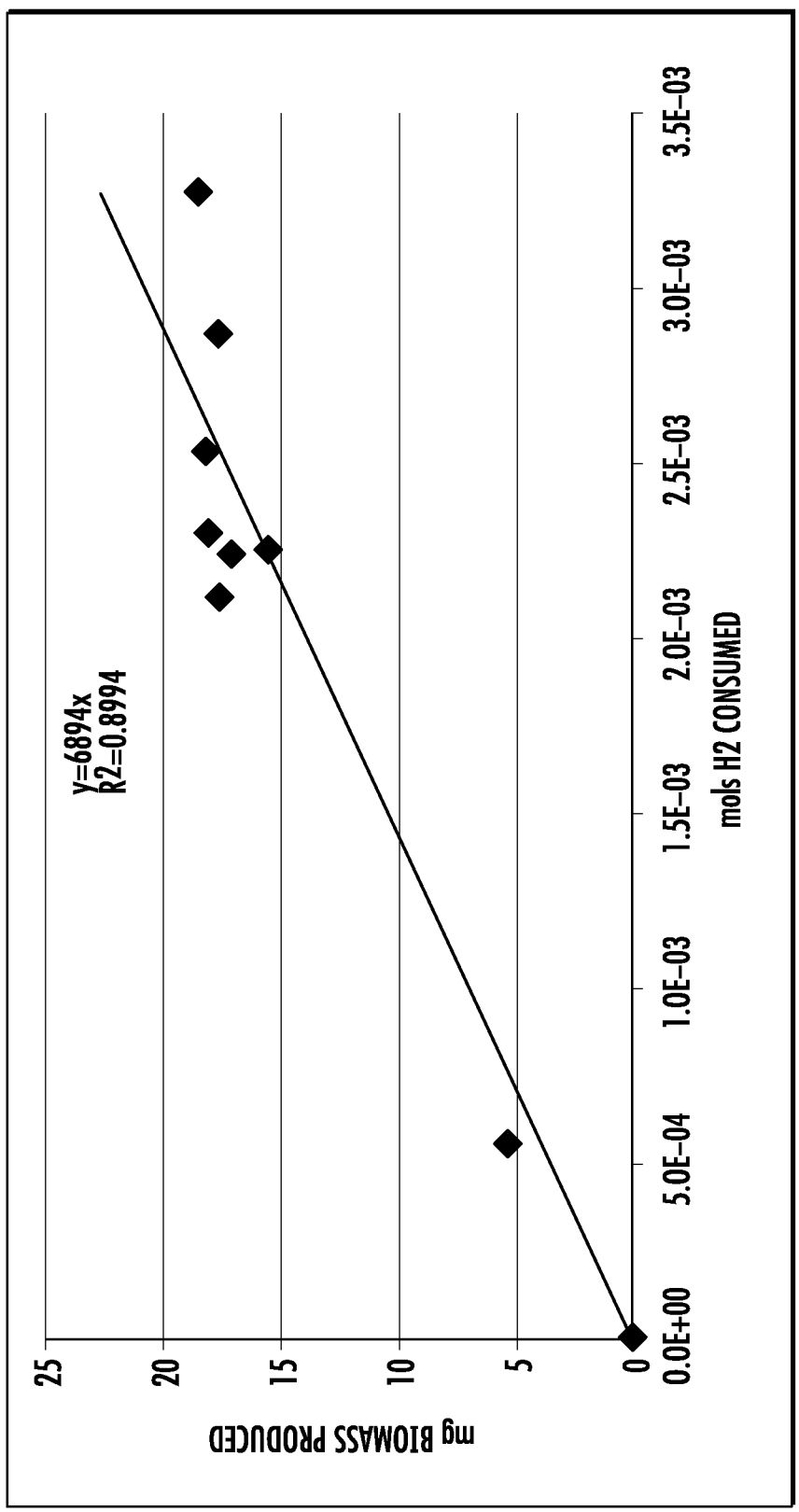
FIG. 8: Cupriavidus necator cell mass produced per moles of $H_2$ consumed, as described in Example 1.

Assuming the ideal gas law (PV=nRT) for the headspace gases, the total moles of gases were calculated, accounting for temperature variation in sample points. The proportion of each respective gas in the headspace of each bottle was determined by GC. Using the gas headspace results and the measured dry weights, the proportionality of cell weight to moles of $H_2$ consumed was determined. FIG. 8 shows the measured dry biomass for each bottle sacrificed, plotted against the moles of $H_2$ consumed, as determined by headspace pressure measurement and GC analysis for each respective bottle. These results indicated that between 6.7 to 7.2 grams of dry cell mass were synthesized per mole of $H_2$ consumed, or 3.3-3.6 grams cell mass per gram of $H_2$.

Example 2

*Cupriavidus necator* strain DSM 531 was grown to 38 grams per liter dry cell density on a mixture of $H_2$, $CO_2$, and $O_2$ gases as the sole source of energy and carbon for growth.

The following protocol was followed for experiments performed using a mixture of gases including $H_2$, $CO_2$, and $O_2$ in a stirred-tank bioreactor.

Apparatus: Culture was grown in batch, using a custom-manufactured 500 mL glass fermenter with PEEK headplate. Temperature and pH were controlled and monitored with a commercial controller (Electrolab, Fermac 360, United Kingdom). A combination of magnetic stir bars and continuous recycle at 280 mL/min were used for mixing. Recycle could be either withdrawn from the bottom liquid section of the reactor and returned to the headspace through sprayers to control foaming or run in reverse to recycle the headspace gas into the bottom of the broth. Gas supply was from compressed $H_2$, compressed $CO_2$ and house air, each regulated to 20 psi. $H_2$ and air were delivered to a flow proportioner (Matheson G2-4D151-E401/E401, 20 psi), which set the relative fraction of the gases. The $H_2$/air gas mix was then delivered to each fermenter through a variable area flow meter; the flow rate to each fermenter of the same $H_2$/air composition could be adjusted by the needle valve of the flow meter. $CO_2$ gas was split and delivered to individual variable area flow meters at each fermenter. The $CO_2$ and $H_2$/air lines tee into a single line delivered to the fermenter. A pressure gauge was used to monitor the gas delivery pressure to the fermenter. Gas was mixed into the fermenter broth via four 2-micron diffusion stones (p/n KEG592, http://morebeer.com/products/diffusion-stone-2-micron-oxygen.html), and vented from the reactor via a condenser to a foam-overflow bottle, then to an exhaust system.

Medium: The medium used for this experiment is described in Example 1. pH control was performed with 2N $NH_4OH$ or 2N NaOH. 2N $NH_4OH$ was prepared from 5 M $NH_4OH$, Fluke 318612 (kept at 4° C.) (120 mL)+autoclaved milliQ-H2O (180 mL).

Autotrophic inoculum: *Cupriavidus necator* DSM 531 inoculum was taken from $H_2/CO_2/O_2$ grown serum bottle culture. Inoculum was prepared from preserved 0.5 mL glycerol stocks stored at −80 C for the DSMZ 531 strain. Revival cultures were started on $H_2/CO_2/O_2$ gas mix per the serum bottle protocol described in Example 1, with 0.5 mL glycerol stock added to 20 mL minimal salts medium (MSM) in a gas tight serum bottle. This initial serum bottle was then subcultured, 1 mL to 20 mL fresh MSM, into 2 serum bottles under the standard $H_2/CO_2/O_2$ gas headspace. These serum bottles were incubated at 30° C., 250 RPM. The initial revival from the glycerol stock on gas took 2 days and the subculture took another day to grow. The two serum bottle cultures were provided as inoculum for the bioreactor. Optical density (OD) of inoculum was taken as well as a sample for DNA analysis. The gas grown inoculum had an OD~1. The fermenter was inoculated to give an initial OD~0.1. In other words, the serum bottle broth was diluted in the bioreactor at a 1:10 ratio. Inoculum was transferred from serum bottles to the bioreactor using a 60 mL syringe. After inoculation, a $T_0$ OD was taken. Generally all OD measurements were performed with a Beckman Coulter DU720 UV/Vis spectrophotometer.

Fermenter Operation:
Base addition—
pH was controlled with 2N $NH_4OH$
Foam Control—
If foaming filled more than ½ headspace, and was not controlled by headspace spraying or recirculation, then anti-foam was used. (A8011, Sigma Antifoam C Emulsion, http://www.sigmaaldrich.com/catalog/product/sigma/a8011?lang=en&region=US)
Nutrient amendment—
In addition to nitrogen nutrient provided by base addition of $NH_4OH$, other mineral nutrients were added during the run so as to prolong growth and prevent any mineral nutrient limitations from occurring.

FIG. 9 gives an example of a growth curve for the knallgas microorganism *Cupriavidus necator* grown on $H_2/CO_2/O_2$ gas substrate according to this protocol. The final OD measured at 650 nm was 132 and the final dry biomass density was 38 grams/liter from growth on $H_2/CO_2/O_2$ gas substrate. Log growth lasted the first day and a half, however the biomass was still accumulating at a linear rate at the termination of the run during day five.

Example 3

Experiments were performed to express a limonene synthase gene in a microbial strain that is capable of growing on gas substrates as a source of energy and carbon for growth and bioproduct production. Limonene synthase was transformed into *Cupriavidus necator* (DSM531) in pBADTcal-RBS under the control of the ara promoter.

Limonene synthase from *Citrus unshiu* (Uniprot Q6F5H3) was codon optimized (LS_Cu, SEQ ID NO:1) for expression in *Cupriavidus necator* (DSM531). The protein sequence was amplified for Golden Gate assembly (Engler, C. & Marillonnet, S. Golden Gate cloning. Methods Mol. Biol. 1116, 119-131 (2014)) with Q5 DNA polymerase (New England Biolabs) using forward and reverse primers SEQ ID NO:2 and SEQ ID NO:3, respectively. The vector pBADTcalRBS (Bi, C. et al. Development of a broad-host synthetic biology toolbox for *Ralstonia eutropha* and its application to engineering hydrocarbon biofuel production. Microb. Cell Fact. 12, 107 (2013)) was similarly amplified using the primers pBADTcalRBS-GG2-F (SEQ ID NO:4) and pBADTcalRBS-GG2-R (SEQ ID NO:5) as the forward and reverse primers, respectively, which exclude the red fluorescent protein coding sequence.

Figure 10:
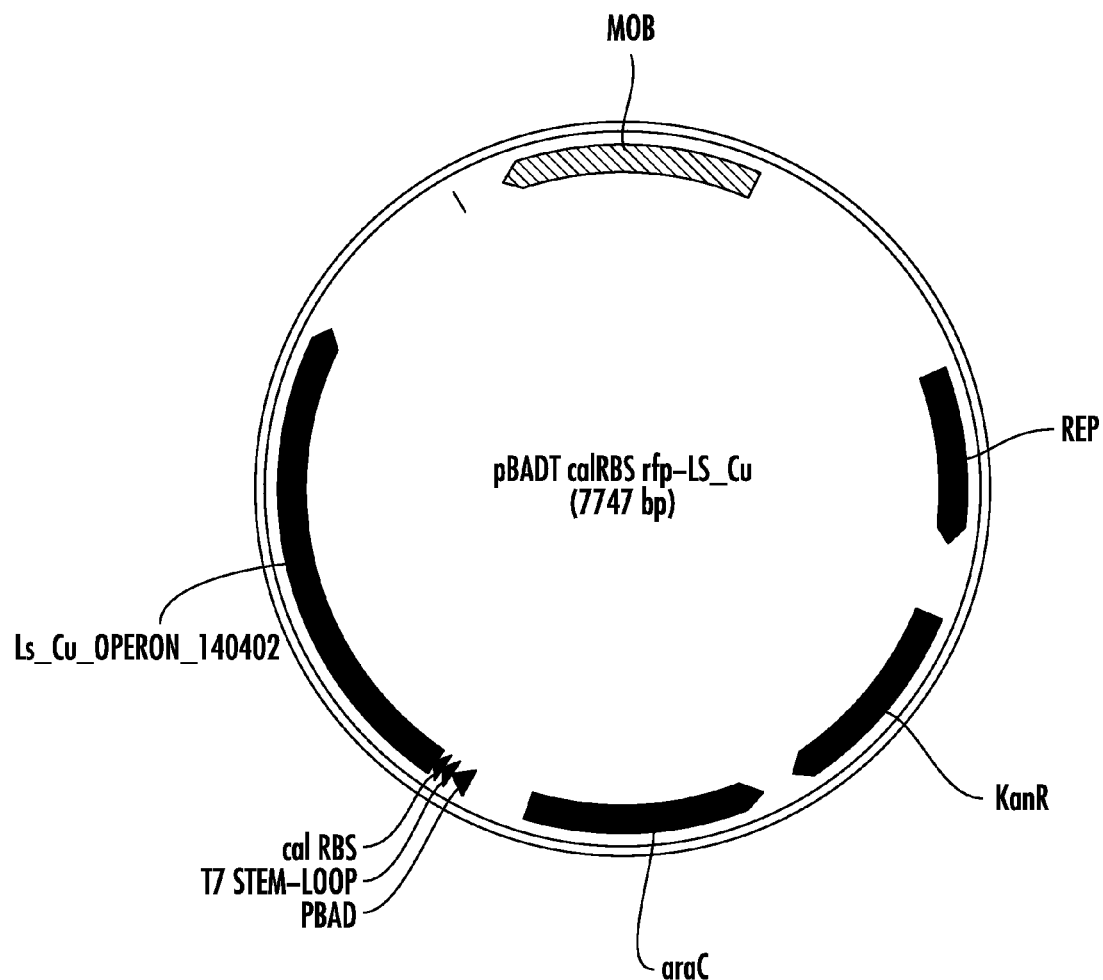
FIG. 10: Plasmid used to express Citrus unshiu limonene synthase, as described in Example 3. The gene coding sequence is SEQ ID NO:1, encoding Uniprot Q6F5H3).

The amplified gene and vector with Golden Gate assembly extensions were assembled using BsaI and T4 DNA ligase (New England Biolabs) and the standard protocol (Engler, C., Gruetzner, R., Kandzia, R. & Marillonnet, S. Golden gate shuffling: a one-pot DNA shuffling method based on type IIs restriction enzymes. PLoS One 4, e5553 (2009)). The assembled plasmid was transformed into *E. coli* for propagation. Correct ligation was confirmed by Sanger sequencing (Quintarabio, Berkeley, Calif.). Plasmid pBADTcalRBS-LS_Cu is depicted in FIG. 10.

*C. necator* competent cells were prepared by incubating a single colony in 3 mL of NR medium (10 g/L polypeptone, 10 g/L yeast extract, 5 g/L beef extract, 5 g/L ammonium sulfate; pH 7.0) at 30° C. overnight. Aliquots of cells (10 µL) were used to inoculate each 1 mL of NR media. The cultures were incubated for six hours. Cells were collected by centrifugation at 14,000 rpm for 1 min and washed 3 times with 1 mL (each) of sterile ice-cold ddH$_2$O. The collected cells were re-suspended in 100 µL of 20% (v/v) sterile glycerol in sterile ice-cold ddH$_2$O and stored at −80° C.

For electroporation, the competent cells were thawed on ice, transferred into a 0.1-cm-wide electroporation cuvette and gently mixed with 1 µg of plasmid DNA. Cells were electroporated using a single-pulse electroporation (11.5 kV/cm, 25 µF and 3-5 ms pulse time). The pulsed cells were transferred into 1 mL of fresh NR medium and incubated for 2 h at 30° C. with shaking Transformants were selected after cultivation for 48 h at 30° C. on LB-agar plate containing kanamycin (200 µg/ml). Individual colonies were selected and patched onto an LB-agar plate containing kanamycin (200 µg/mL). Transformation was confirmed by isolating plasmid DNA from a 3-mL overnight LB culture containing 200 µg/mL kanamycin and sequencing the isolated plasmid. Untransformed *C. necator* (DSM531) cells did not grow under those conditions.

Cultures of two *C. necator* transformants with pBADTcalRBS-LS_Cu were grown as follows: A small amount of cells from the patch plate were used to inoculate 3 mL of LB media containing 200 µg/mL kanamycin. The culture was incubated overnight at 30° C. A 50-4 aliquot of the overnight culture was used to inoculate 5 mL of LB containing 200 µg/mL kanamycin in a glass culture tube. The media was overlaid with 500 µL of dodecane and incubated at 30° C. with shaking (250 rpm). After six hours of incubation, arabinose was added to 0.1% (w/v) or 0.5% (w/v). A 100-µL aliquot of dodecane was removed at 0, 24, 72, and 144 hours post-induction. After the 144 h timepoint was collected, 200 µL of fresh dodecane were added to the culture. At 192 hours post-induction, a final aliquot of 100 µL was collected.

Figure 11:
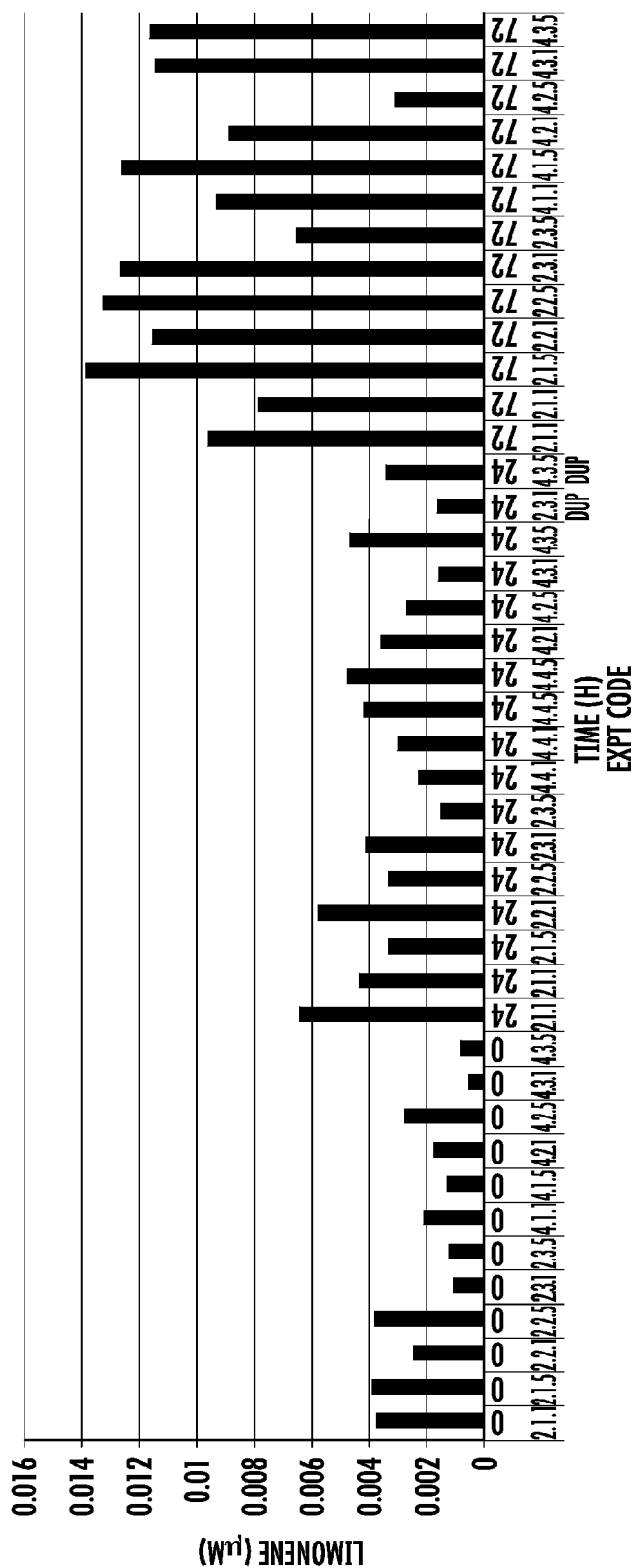
FIG. 11: Detection of limonene as described in Example 3. The x-axis is labeled with time (h), (transformant). (replicate).(arabinose concentration).

Samples were prepared for analysis by diluting 50 µL of the dodecane layer removed from cultures in 300 µL of ethyl acetate. Limonene was detected on an Agilent 6890N GC/MS with a 5975C MS detector (Santa Clara, Calif.). Column used was a Cyclosil B (J&W Scientific, 30 m×320 µm), injection temperature 250° C. operating in splitless mode. Column flow rate was 1 ml/min, initial temperature 60° C., ramp 10° C./min to 135, and ramp 30° C./min to 200. Data acquisition was in SIM mode, ions monitored were 68 and 93. Quantification was accomplished by running known standards of D-Limonene (Sigma). Limonene produced by the cultures is shown in FIG. 11.

```
>LS_Citrus_unshiu_optimized 1821 bp
Limonene synthase derived from Satsuma mandarin
optimized for expression in R. eutropha
                                     SEQ ID NO: 1
ATGAGCTCGTGCATCAATCCCAGCACCCTGGTGACCTCGGTGAATGG
CTTCAAGTGCCTGCCCCTGGCCACCAACAAGGCGGCGATCCGCATCA
TGGCGAAGAATAAGCCCGTGCAGTGCCTGGTGTCCGCCAAGTACGAT
AACCTGACCGTGGATCGCCGCTCCGCCAATTACCAGCCGTCGATCTG
GGACCACGACTTCCTCCAGAGCCTGAACTCCAACTACACCGACGAAA
CGTACAAGCGCCGCGAGGAGGAACTGAAAGGCAAGGTCATGACCACC
ATCAAGGACGTGACGGAGCCGCTGAACCAGCTGGAACTGATCGACTC
GCTCCAGCGCCTGGGCCTGGCGTACCACTTTGAAACCGAGATTCGCA
ACATCCTCCATGACATCTACAACAGCAACAACGACTACGTCTGGCGG
AAGGAAAACCTGTACGCAACGAGCCTGGAGTTTCGGCTGCTCCGCCA
GCATGGCTATCCGGTGTCGCAAGAAGTGTTCAACGGCTTCAAGGACG
ACCAAGGCGGCTTCATCTGCGACGACTTCAAGGGCGTCCTGTCCCTG
CACGAGGCCAGCTACTTCTCGCTGGAGGGCGAATCGATCATGGAGGA
GGCATGGCAGTTCACCTCGAAGCATCTGAAGGAAGTCATGATCTCGA
AGTCCAAGCAGGGCGACGTGTTCGTGGCCGAGCAGGCCAAGCGGGGC
CTGGAGCTGCCGCTGCACTGGAAGGTGCCGATGCTGGAAGCCCGCTG
GTTCATCGACGTGTACGAGAAGCGCGAGGACAAGAATCACCTGCTGC
TGGAGCTGGCCAAACTGGAGTTCAACGTGCTCCAGGCGATCTATCAA
GAGGAACTGAAGGATGTCTCGCGCTGGTGGAAGGATATTGGCCTGGG
CGAGAAGCTGTCGTTTGCCCGCGACAGCCTGGTGGCGTCCTTCGTCT
GGTCGATGGGCATCGTGTTCGAGCCCCAGTTCGCCTATTGTCGCCGC
ATCCTCACCATCACCTTCGCGCTGATCTCGGTGATCGACGACATCTA
CGACGTCTATGGCACGCTGGATGAACTGGAGCTGTTCGCCGATGCCG
TGGAGCGCTGGGATATCAACTACGCCCTGAATCACCTGCCGGACTAT
ATGAAAATCTGCTTTCTGCCCTGTACAACCTGGTCAACGAATTTAC
GTACTATGTCCTGAAGCAGCAGGACTTCGACATCCTGCGCTCGATTA
AGAACGCGTGGCTGCGCAACATCCAGGCGTACCTGGTCGAAGCGAAG
TGGTACCATGGGAAGTATACGCCGACCCTGGGCGAGTTCCTGGAAAA
CGGCCTGGTGAGCATCGGCGGCCCGATGGTGACGATGACGGCCTACC
TCAGCGGGACCAACCCGATCATCGAAAAGGAGCTGGAGTTTCTGGAA
AGCAATCAGGATATCAGCCACTGGTCGTTCAAAATCCTGCGCCTCCA
GGACGACCTGGGCACCAGCTCGGACGAGATTCGCCGGGGCGACGTCC
CCAAGAGCATCCAGTGCTACATGCACGAAACGGGCGCATCGGAGGAG
GTGGCGCGCGAGCACATCAAGGACATGATGCGCCAGATGTGGAAGAA
GGTGAACGCGTATCGCGCGGACAAGGATTTCCCGCTGTCGCAGACCA
CGGTGGAGTTCATCCTGAACGTGGTGCGGGTGAGCCACTTCATGTAC
CTGCATGGGGATGGGCATGGCGCCCAGAACCAGGAAACCATGGACGT
```

CGTGTTCACCCTGCTGTTCCAGCCGATCCCGCTCGACGACAAGCACA

TCGTGGCCACCTCCTCGCCGGTCACCAAGGGCTAA

>LS_Cu Golden Gate forward primer
SEQ ID NO: 2
CACACCAGGTCTCACTAAATGAGCTCGTGCATCAATCC >LS_Cu Golden Gate reverse primer
SEQ ID NO: 3
CACACCAGGTCTCACATTTTAGCCCTTGGTGACCG >pBADTcalRBS Golden Gate forward primer
(pBADTcalRBS-GG2-F)
As described in DNA Cloning and Assembly
Methods, Methods in Molecular Biology Volume
1116, 2014, pp 119-131, Date: 10 Dec. 2013
SEQ ID NO: 4
CACACCAGGTCTCATTAGATTGTGTACTCCTTCTTCTGTTCC >pBADTcalRBS Golden Gate reverse primer
(pBADTcalRBS-GG2-R)
As described in DNA Cloning and Assembly
Methods, Methods in Molecular Biology Volume
1116, 2014, pp 119-131, Date: 10 Dec. 2013
SEQ ID NO: 5
CACACCAGGTCTCAAATGTGAAGGTCGTCACTCCAC Example 4

*Cupriavidus necator* DSM 531 was transformed with the plasmid pBBR1MCS-2 described in Kovach et al. (1995 *Gene* 166 (1): 175-176), which conferred antibiotic resistance. The *Cupriavidus necator* was grown on LB medium and a Kanamycin concentration of 400 µg/mL. The plasmid contains the IncQ like replication gene, Mob gene that is mobilized when the RK2 transfer functions are provided in trans, kanamycin resistance gene, LacZ operon and the multiple cloning sites.

The inoculation volume was 100 µL each replicate from glycerol stock stored at −80° C. of *Cupriavidus necator* DSM 531 transformed with plasmid pBBR1MCS-2 into 50 mL of LB plus kanamycin at 400 µg/mL in 250 mL Erlenmeyer flasks. The flasks were incubated for 30 hours, at 30° C., 250 rpm. Cultures were harvested, OD measured, and then centrifuged. The two replicates grew to OD600 of 2.6 and 3.2.

The cell mass was separated from the supernatant of the culture broth by centrifugation. After centrifuging the wet pellet weights were 0.79 and 0.77 grams for the replicates with OD 2.6 and 3.2 respectively. This corresponds to approximately 0.20 and 0.19 grams dry cell weight respectively.

The supernatant was split into two fractions, one was extracted with 2×5 mL chloroform and the other 2×5 mL hexane. The solvent was added, the mixture vortexed for 1 minute and centrifuged for 15 minutes at 2500 rpm. The solvent layer was removed, dried under nitrogen at 37° C., and stored at −20° C. until analysis. An aliquot of the wet pellet was extracted with 10:5:4 mixture of methanol:chloroform:water. Lipids were applied to Silica-60 columns, and different lipid groups were separated and eluted from the column with organic solvents including chloroform and methanol. Separated aliquots were dried under nitrogen at 37° C. and stored at −20° C. until analysis.

Gas Chromatography and Mass Spectrometry (GC/MS) analysis: compounds were detected on an Agilent 6890N GC/MS (Agilent, Santa Clara, Calif.) on a HP1 60 m column×0.25 mm ID. Samples were placed in GC vial inserts with a final volume in chloroform of 50 uL. Samples were injected using an automatic injector, the injector temperature was 250° C. and was run in split mote (8:1) with an initial GC temperature of 100° C., ramp at 10° C./min to a final temp of 150° C., then a ramp of 3° C./min to 250° C., finally a 10° C./min ramp to 312° C. which is held for 7 min. Peak ID was accomplished through a NIST08 library and quantification through a standard curve prepared with hexadecane.

The triterpene squalene was detected by GC/MS in the lipid extract from the wet pellet of cell mass generated by each experimental replicate. Squalene was not detected in the supernatant. For the first and second replicates the squalene peak was at a retention time of 28.338 and 28.345 in the first and second replicates shown in FIGS. 12 and 13, respectively. In both replicates Squalene comprised the majority of the hydrocarbons detected.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A composition comprising a non-naturally occurring knallgas microorganism that is capable of growing on a gaseous substrate as a carbon and energy source, and a culture medium in contact with a gaseous substrate that comprises: an inorganic carbon source comprising $CO_2$ and/or CO; an inorganic gaseous electron donor comprising $H_2$ and/or CO; and an inorganic gaseous electron acceptor comprising $O_2$, wherein the gaseous substrate comprises at least 2% $O_2$,
   wherein said microorganism is a *Cupriavidus* sp. or *Ralstonia* sp. that comprises at least one exogenous nucleic acid encoding a limonene synthase enzyme, and
   wherein the gaseous substrate is utilized by the microorganism for production of limonene in the culture medium using a combination of the electron donor and the electron acceptor as an energy source.

2. The composition according to claim 1, wherein said gaseous substrate comprises $CO_2$ as a carbon source, $H_2$ as an electron donor, and $O_2$ as an electron acceptor.

3. The composition according to claim 1, wherein said gaseous substrate comprises $H_2$ and $O_2$ as an energy source.

4. The composition according to claim 1, wherein said gaseous substrate comprises CO and $O_2$; $CO_2$, $H_2$ and $O_2$; CO, $CO_2$, $H_2$, and $O_2$; or CO, $H_2$, and $O_2$.

5. The composition according to claim 1, wherein said microorganism produces limonene when cultured in the presence of the gas substrate under conditions suitable for growth of the microorganism and production of bioproducts.

6. The composition of claim 1, wherein said microorganism comprises an exogenous nucleic acid encoding an efflux pump.

7. The composition of claim 6, wherein said microorganism produces limonene, and wherein a greater amount of limonene is transported out of the microorganism and into a growth medium in which the microorganism is cultured than an equivalent microorganism that does not comprise the exogenous nucleic acid encoding an efflux pump.

8. The composition of claim 6, wherein said exogenous nucleic acid encoding an efflux pump encodes an efflux pump from *A. borkumensis* or *E. coli* AcrB protein.

9. The composition of claim 1, wherein said microorganism further comprises the ability to overexpress a native efflux pump.

10. The composition of claim 9, wherein said microbial organism overexpresses a *Cupriavidus* native efflux pump.

11. The composition of claim 9, wherein said microorganism produces limonene, and wherein a greater amount of limonene is transported out of the microorganism and into the culture medium than an equivalent microorganism that does not comprise the ability to overexpress the native efflux pump.

12. The composition of claim 1, wherein the limonene synthase is encoded by a coding sequence that is carried on a broad-host-range plasmid.

13. The composition of claim 12, wherein the limonene synthase coding sequence is under the control of a non-native inducible promoter.

14. The composition of claim 1, wherein the gaseous substrate comprises 2% to 6% $O_2$.

15. The composition of claim 1, wherein the energy source comprising a combination of the gaseous electron donor and gaseous electron acceptor is utilized by the microorganism for production of intracellular energy carriers comprising adenosine-5-triphosphate (ATP), and wherein limonene is biosynthesized by the microorganism from the inorganic carbon source utilizing endogenous Calvin-Benson and methyl-erythritol-4-phosphate (MEP) pathways.

16. The composition of claim 1, wherein limonene is synthesized by the microorganism via a single-step reaction downstream of geranyl pyrophosphate (GPP) catalyzed by the limonene synthase enzyme that is encoded by the exogenous nucleic acid.

17. The composition of claim 16, wherein the exogenous nucleic acid encodes a limonene synthase enzyme having the amino acid sequence of the *Citrus unshiu* limonene synthase enzyme.

18. The composition of claim 1, wherein the microorganism is *Cupriavidus necator* or *Cupriavidus metallidurans*.

19. The composition of claim 17, wherein the microorganism is *Cupriavidus necator* strain DSM 531.

20. The composition of claim 1, wherein the knallgas microorganism produces squalene.

21. A method for producing limonene, comprising culturing the non-naturally occurring microorganism in the composition according to claim 1 in a bioreactor that comprises the gaseous substrate and the culture medium, wherein the culture medium comprises other nutrients for growth and bioproduct production, under conditions that are suitable for growth of the microorganism and production of limonene, wherein said microorganism produces limonene.

22. The method of claim 21, wherein the gaseous substrate comprises 2% to 6% $O_2$.

23. A method according to claim 21, wherein limonene is recovered from the surface of the culture medium at the interface between the liquid and gas phases in the bioreactor.

24. A method according to claim 21, wherein the culture medium is a biphasic liquid medium that comprises an aqueous phase and an organic phase, and wherein limonene is recovered in the organic phase.

25. The method of claim 21, wherein the limonene is recovered from the culture medium and is dimerized to produce jet fuel.

26. The method of claim 21, wherein limonene is recovered from the culture medium and is converted to terephthalic acid.

27. A method according to claim 21, wherein said microorganism produces limonene chemoautotrophically.

\* \* \* \* \*

SEQUENCE LISTING

<160> NUMBER OF SEQ ID NOS: 5

<210> SEQ ID NO 1
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgagctcgt gcatcaatcc cagcaccctg gtgacctcgg tgaatggctt caagtgcctg      60
cccctggcca ccaacaaggc ggcgatccgc atcatggcga agaataagcc cgtgcagtgc     120
ctggtgtccg ccaagtacga taacctgacc gtggatcgcc gctccgccaa ttaccagccg     180

```
tcgatctggg accacgactt cctccagagc ctgaactcca actacaccga cgaaacgtac      240
aagcgccgcg aggaggaact gaaaggcaag gtcatgacca ccatcaagga cgtgacggag      300
ccgctgaacc agctggaact gatcgactcg ctccagcgcc tgggcctggc gtaccacttt      360
gaaaccgaga ttcgcaacat cctccatgac atctacaaca gcaacaacga ctacgtctgg      420
cggaaggaaa acctgtacgc aacgagcctg gagtttcggc tgctccgcca gcatggctat      480
ccggtgtcgc aagaagtgtt caacggcttc aaggacgacc aaggcggctt catctgcgac      540
gacttcaagg gcgtcctgtc cctgcacgag ccagctact tctcgctgga gggcgaatcg       600
atcatggagg aggcatggca gttcacctcg aagcatctga aggaagtcat gatctcgaag      660
tccaagcagg gcgacgtgtt cgtggccgag caggccaagc ggggcctgga gctgccgctg      720
cactggaagg tgccgatgct ggaagcccgc tggttcatcg acgtgtacga aagcgcgag       780 gacaagaatc acctgctgct ggagctggcc aaactggagt tcaacgtgct ccaggcgatc      840 tatcaagagaa aactgaagga tgtctcgcgc tggtggaagg atattggcct gggcgagaag    900
ctgtcgtttg cccgcgacag cctggtggcg tccttcgtct ggtcgatggg catcgtgttc      960
gagccccagt tcgcctattg tcgccgcatc ctcaccatca ccttcgcgct gatctcggtg     1020
atcgacgaca tctacgacgt ctatggcacg ctggatgaac tggagctgtt cgccgatgcc     1080
gtggagcgct gggatatcaa ctacgccctg aatcacctgc cggactatat gaaaatctgc     1140
tttctggccc tgtacaacct ggtcaacgaa tttacgtact atgtcctgaa gcagcaggac     1200
ttcgacatcc tgcgctcgat taagaacgcg tggctgcgca acatccaggc gtacctggtc     1260
gaagcgaagt ggtaccatgg gaagtatacg ccgaccctgg gcgagttcct ggaaaacggc     1320
ctggtgagca tcggcggccc gatggtgacg atgacggcct acctcagcgg gaccaacccg     1380
atcatcgaaa aggagctgga gtttctggaa agcaatcagg atatcagcca ctggtcgttc     1440
aaaatcctgc gcctccagga cgacctgggc accagctcgg acgagattcg ccggggcgac     1500
gtccccaaga gcatccagtg ctacatgcac gaaacgggcg catcggagga ggtggcgcgc     1560
gagcacatca aggacatgat gcgccagatg tggaagaagg tgaacgcgta tcgcgcggac     1620
aaggatttcc cgctgtcgca gaccacggtg gagttcatcc tgaacgtggt gcgggtgagc     1680
cacttcatgt acctgcatgg ggatgggcat ggcgcccaga accaggaaac catggacgtc     1740
gtgttcaccc tgctgttcca gccgatcccg ctcgacgaca gcacatcgt ggccacctcc      1800 tcgccggtca ccaagggcta a                                               1821
```

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 2

```
cacaccaggt ctcactaaat gagctcgtgc atcaatcc                               38
```

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 3
cacaccaggt ctcacatttt agcccttggt gaccg                                 35

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacaccaggt ctcattagat tgtgtactcc ttcttctgtt cc                         42

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cacaccaggt ctcaaatgtg aaggtcgtca ctccac                                36
```